(12) United States Patent
Takahashi et al.

(10) Patent No.: US 9,517,278 B2
(45) Date of Patent: Dec. 13, 2016

(54) COMPOUND AND PHOTOACOUSTIC IMAGING CONTRAST MEDIUM CONTAINING THE COMPOUND

(71) Applicant: CANON KABUSHIKI KAISHA, Tokyo (JP)

(72) Inventors: Atsushi Takahashi, Kyoto (JP); Fumio Yamauchi, Kyoto (JP); Masato Minami, Kawasaki (JP); Satoshi Ogawa, Kyoto (JP); Kengo Kanazaki, Kyoto (JP); Satoshi Yuasa, Yokohama (JP)

(73) Assignee: CANON KABUSHIKI KAISHA, Tokyo (JP)

( * ) Notice: Subject to any disclaimer, the term of this patent is extended or adjusted under 35 U.S.C. 154(b) by 22 days.

(21) Appl. No.: 14/413,399

(22) PCT Filed: Jul. 17, 2013

(86) PCT No.: PCT/JP2013/004368
§ 371 (c)(1),
(2) Date: Jan. 7, 2015

(87) PCT Pub. No.: WO2014/013732
PCT Pub. Date: Jan. 23, 2014

(65) Prior Publication Data
US 2015/0165071 A1 Jun. 18, 2015

(30) Foreign Application Priority Data
Jul. 20, 2012 (JP) ................. 2012-161641

(51) Int. Cl.
*A61K 49/22* (2006.01)
*A61K 49/00* (2006.01)

(52) U.S. Cl.
CPC ......... *A61K 49/221* (2013.01); *A61K 49/0034* (2013.01)

(58) Field of Classification Search
CPC ....... A61K 49/00; A61K 49/22; A61K 49/221
See application file for complete search history.

(56) References Cited

U.S. PATENT DOCUMENTS

| | | |
|---|---|---|
| 5,968,479 A | 10/1999 | Ito et al. |
| 6,662,040 B1 | 12/2003 | Henrichs et al. |
| 7,883,693 B2 | 2/2011 | Sehl et al. |
| 8,491,908 B2 | 7/2013 | Kanazaki et al. |
| 8,753,608 B2 | 6/2014 | Tabata et al. |
| 2005/0277104 A1 | 12/2005 | Morimoto et al. |
| 2011/0117024 A1 | 5/2011 | Sinko et al. |
| 2011/0294987 A1 | 12/2011 | Kanazaki et al. |
| 2013/0209367 A1 | 8/2013 | Ito et al. |
| 2013/0224121 A1 | 8/2013 | Fukui et al. |
| 2014/0227195 A1 | 8/2014 | Tabata et al. |

FOREIGN PATENT DOCUMENTS

| | | |
|---|---|---|
| WO | 98/57667 A1 | 12/1998 |
| WO | 2004/010807 A1 | 2/2004 |
| WO | 2007/109364 A2 | 9/2007 |
| WO | 2009/123768 A2 | 10/2009 |
| WO | 2014/013729 A1 | 1/2014 |
| WO | 2014/013730 A1 | 1/2014 |

OTHER PUBLICATIONS

Xueding Wang et al., Noninvasive photoacoustic angiography of animal brains in vivo with near-infrared light and an optical contrast agent, Optics Letters, vol. 29(7), 730-732, 2004.*
Yamauchi et al., U.S. Appl. No. 14/413,400, filed Jan. 7, 2015.
Takahashi et al., U.S. Appl. No. 14/413,402, filed Jan. 7, 2015.
Xueding Wang et al., "Noninvasive Photoacoustic Angiography of Animal Brains In Vivo with Near-Infrared Light and an Optical Contrast Agent," 29(7) Opt. Lett. 730-732 (Apr. 2004).

\* cited by examiner

*Primary Examiner* — Michael G Hartley
*Assistant Examiner* — Jagadishwar Samala
(74) *Attorney, Agent, or Firm* — Fitzpatrick, Cella, Harper & Scinto

(57) ABSTRACT

The present invention provides a photoacoustic imaging contrast medium which exhibits a high degree of accumulation into a tumor even when some extent of time has passed after performing administration and which facilitates an increase in the intensity of photoacoustic signal produced by the tumor.
A compound produced by covalent-bonding of an organic dye which absorbs light in the near-infrared wavelength region and a PEG having a branch.

9 Claims, 1 Drawing Sheet

COMPOUND AND PHOTOACOUSTIC IMAGING CONTRAST MEDIUM CONTAINING THE COMPOUND

TECHNICAL FIELD

The present invention relates to a compound and a photoacoustic imaging contrast medium containing the above-described compound.

BACKGROUND ART

A photoacoustic tomography (hereafter may be abbreviated to PAT) apparatus has been known as one of apparatuses to visualize the information of the inside of a living body. In a measurement by using the PAT apparatus, an arithmetic image of the matter distribution in the inside of a subject to be measured can be obtained by measuring the intensity and the production time of photoacoustic signals produced by a substance (light absorber), which has absorbed light, in the inside of the subject to be measured when the subject to be measured is irradiated with the light.

Here, any substance can be used as the light absorber insofar as the substance produces an acoustic wave because of absorption of the light in a living body. For example, it is possible that a blood vessel, a malignant tumor, or the like in a human body is employed as a light absorber. In addition, it is also possible that molecules of Indocyanine Green (hereafter may be abbreviated to ICG) and the like are administered to a body and are utilized as contrast media. ICG can be favorably used as a contrast medium in the PAT apparatus because of a small irradiation influence on a human body and high absorption of light, which is in the near-infrared wavelength region and which has a high permeability into a living body. Meanwhile, in the present specification, ICG refers to a compound represented by the following structure.

[Chem. 1]

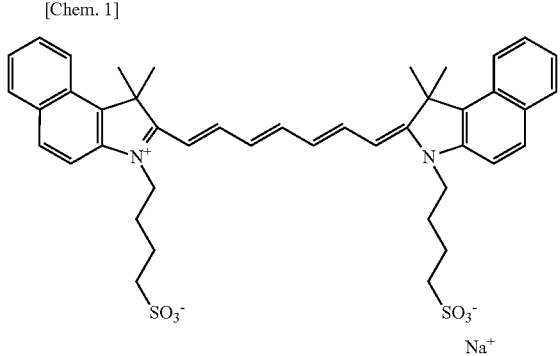

In this regard, the counter ion is not necessarily $Na^+$, but any counter ion, e.g., $H^+$ or $K^+$, may be employed.

However, it has been known that the half-life of ICG in blood is about several minutes and, therefore, is very short.

NPL 1 reports an example in which photoacoustic imaging of cerebral blood vessel of a rat has been performed by using ICG alone. According to this report, the photoacoustic signal intensity is reduced to the same level as that of the blood several tens of minutes after ICG have been administered to the blood alone and, therefore, it is indicated that the administered substance disappears from the blood promptly after administration.

As described above, ICG disappears from the blood several tens of minutes after being administered to the blood alone and it is considered that the degree of accumulation into a tumor is low when some time has passed after administration.

CITATION LIST

Non Patent Literature

NPL 1: Optics Letters, 29(7), 730 (2004)

SUMMARY OF INVENTION

Technical Problem

Accordingly, the present invention provides a compound which exhibits a high degree of accumulation into a tumor even when some time has passed after administration and which facilitates an increase in the intensity of photoacoustic signal produced by the tumor.

Solution to Problem

A compound according to an aspect of the present invention is represented by any one of the following formula (1) to formula (6).

[Chem. 2]

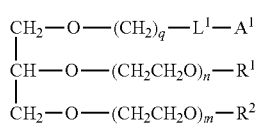

(1)

[Chem. 3]

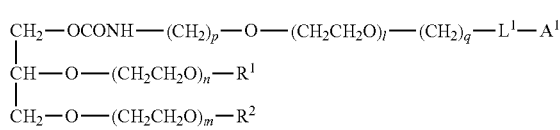

(2)

[Chem. 4]

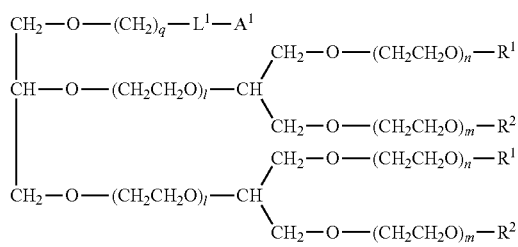

(3)

[Chem. 5]

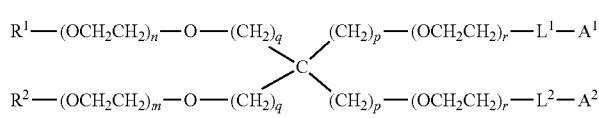

(4)

[Chem. 6]

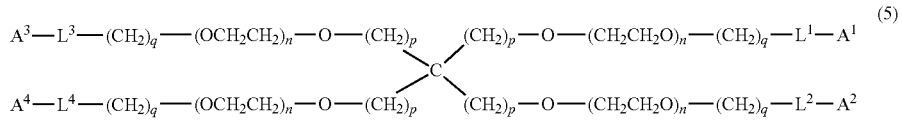

(5)

[Chem. 7]

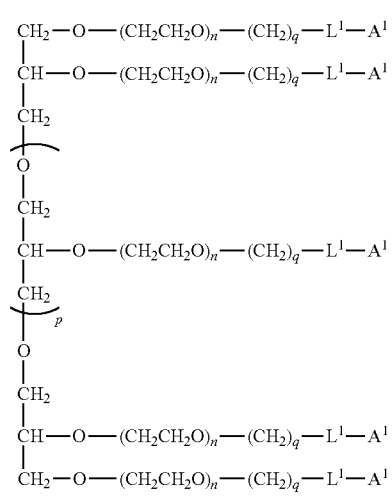

(6)

In the above-described formula (1), $A^1$ represents an organic dye which absorbs light in the near-infrared wavelength region, $L^1$ represents a linker part which is any one of —NH—, —CO—, —O—, and —S— or which contains at least one of —NH—, —CO—, —O—, and —S—, q represents an integer of 1 to 5, m and n represent independently an integer of 10 or more and 2,500 or less, and $R^1$ and $R^2$ represent independently an alkyl group having the carbon number of 1 to 5.

In the formula (2), $A^1$ represents an organic dye which absorbs light in the near-infrared wavelength region, $L^1$ represents a linker part which is any one of —NH—, —CO—, —O—, and —S— or which contains at least one of —NH—, —CO—, —O—, and —S—, p and q represent independently an integer of 1 to 5, l, m, and n represent independently an integer of 10 or more and 2,500 or less, and $R^1$ and $R^2$ represent independently an alkyl group having the carbon number of 1 to 5.

In the formula (3), $A^1$ represents an organic dye which absorbs light in the near-infrared wavelength region, $L^1$ represents a linker part which is any one of —NH—, —CO—, —O—, and —S— or which contains at least one of —NH—, —CO—, —O—, and —S—, q represents an integer of 1 to 5, l, m, and n represent independently an integer of 10 or more and 2,500 or less, and $R^1$ and $R^2$ represent independently an alkyl group having the carbon number of 1 to 5.

In the formula (4), $A^1$ and $A^2$ represent independently an organic dye which absorbs light in the near-infrared wavelength region, $L^1$ and $L^2$ represent independently a linker part which is any one of —NH—, —CO—, —O—, and —S— or which contains at least one of —NH—, —CO—, —O—, and —S—, p, q, and r represent independently an integer of 1 to 5, m and n represent independently an integer of 10 or more and 2,500 or less, and $R^1$ and $R^2$ represent independently an alkyl group having the carbon number of 1 to 5.

In the formula (5), $A^1$, $A^2$, $A^3$, and $A^4$ represent independently an organic dye which absorbs light in the near-infrared wavelength region, $L^1$, $L^2$, $L^3$, and $L^4$ represent independently a linker part which is any one of —NH—, —CO—, —O—, and —S— or which contains at least one of —NH—, —CO—, —O—, and —S—, p and q represent independently an integer of 1 to 5, and n represents an integer of 10 or more and 2,500 or less.

In the formula (6), $A^1$ represents an organic dye which absorbs light in the near-infrared wavelength region, $L^1$ represents a linker part which is any one of —NH—, —CO—, —O—, and —S— or which contains at least one of —NH—, —CO—, —O—, and —S—, p and q represent independently an integer of 1 to 5, and n represents an integer of 10 or more and 2,500 or less.

A compound according to another aspect of the present invention is produced by covalent-bonding of an organic dye which absorbs light in the near-infrared wavelength region and a polyethylene glycol having a branch, wherein the above-described polyethylene glycol having a branch is represented by any one of the following formulae (9) to (14).

[Chem. 8]

(9)

[Chem. 9]

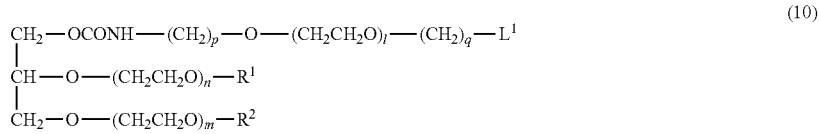

(10)

[Chem. 10]

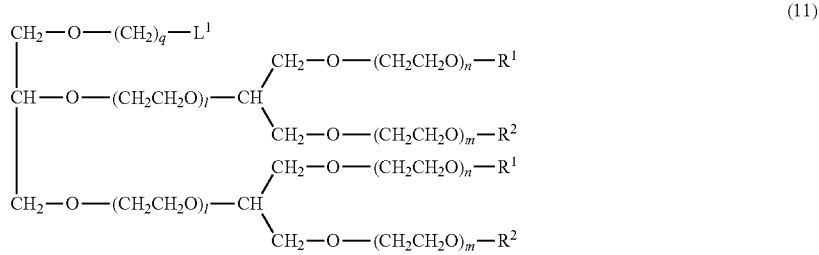

(11)

[Chem. 11]

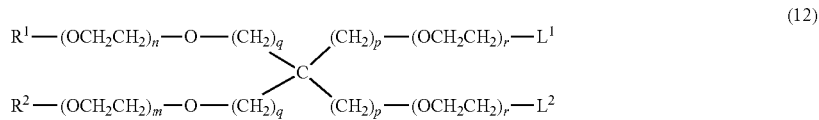

(12)

[Chem. 12]

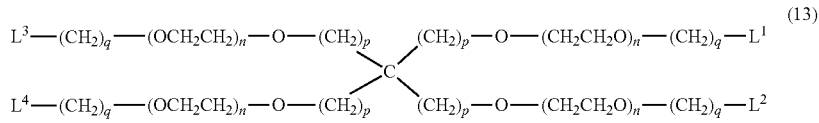

(13)

-continued

[Chem. 13]

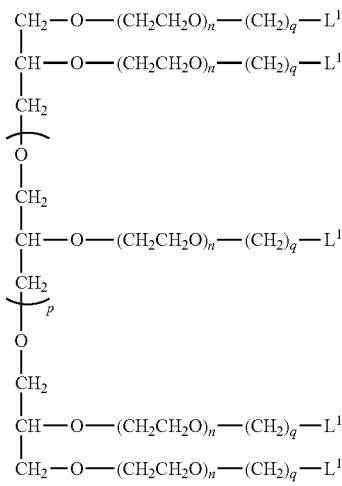

(14)

In the above-described formula (9), $L^1$ includes at least one of —$NH_2$, —COOH, —OH, —SH, a sulfhydryl group, an epoxy group, a glycidyl group, a N-succinimidyloxy group, a N-sulfosuccinimidyloxy group, and a N-maleimidoalkyl group, q represents an integer of 1 to 5, m and n represent independently an integer of 10 or more and 2,500 or less, and $R^1$ and $R^2$ represent independently an alkyl group having the carbon number of 1 to 5.

In the above-described formula (10), $L^1$ includes at least one of —$NH_2$, —COOH, —OH, —SH, a sulfhydryl group, an epoxy group, a glycidyl group, a N-succinimidyloxy group, a N-sulfosuccinimidyloxy group, and a N-maleimidoalkyl group, p and q represent independently an integer of 1 to 5, l, m, and n represent independently an integer of 10 or more and 2,500 or less, and $R^1$ and $R^2$ represent independently an alkyl group having the carbon number of 1 to 5.

In the above-described formula (11), $L^1$ includes at least one of —$NH_2$, —COOH, —OH, —SH, a sulfhydryl group, an epoxy group, a glycidyl group, a N-succinimidyloxy group, a N-sulfosuccinimidyloxy group, and a N-maleimidoalkyl group, q represents an integer of 1 to 5, l, m, and n represent independently an integer of 10 or more and 2,500 or less, and $R^1$ and $R^2$ represent independently an alkyl group having the carbon number of 1 to 5.

In the above-described formula (12), $L^1$ and $L^2$ include independently at least one of —$NH_2$, —COOH, —OH, —SH, a sulfhydryl group, an epoxy group, a glycidyl group, a N-succinimidyloxy group, a N-sulfosuccinimidyloxy group, and a N-maleimidoalkyl group, p, q, and r represent independently an integer of 1 to 5, m and n represent independently an integer of 10 or more and 2,500 or less, and $R^1$ and $R^2$ represent independently an alkyl group having the carbon number of 1 to 5.

In the above-described formula (13), $L^1$, $L^2$, $L^3$, and $L^4$ include independently at least one of —$NH_2$, —COOH, —OH, —SH, a sulfhydryl group, an epoxy group, a glycidyl group, a N-succinimidyloxy group, a N-sulfosuccinimidyloxy group, and a N-maleimidoalkyl group, p and q represent independently an integer of 1 to 5, and n represents an integer of 10 or more and 2,500 or less.

In the above-described formula (14), $L^1$ includes at least one of —$NH_2$, —COOH, —OH, —SH, a sulfhydryl group, an epoxy group, a glycidyl group, a N-succinimidyloxy group, a N-sulfosuccinimidyloxy group, and a N-maleimidoalkyl group, p and q represent independently an integer of 1 to 5, and n represents independently an integer of 10 or more and 2,500 or less.

Advantageous Effects of Invention

According to aspects of the present invention, the compound has a structure in which a polyethylene glycol (hereafter may be abbreviated to PEG) having a branch and an organic dye, e.g., ICG, which absorbs light in the near-infrared wavelength region are covalent-bonded. Consequently, the degree of accumulation into a tumor is high and the intensity of photoacoustic signals produced by the tumor is large as compared with those in the case where ICG is administered to a living body alone.

DESCRIPTION OF EMBODIMENTS

Figure 1:
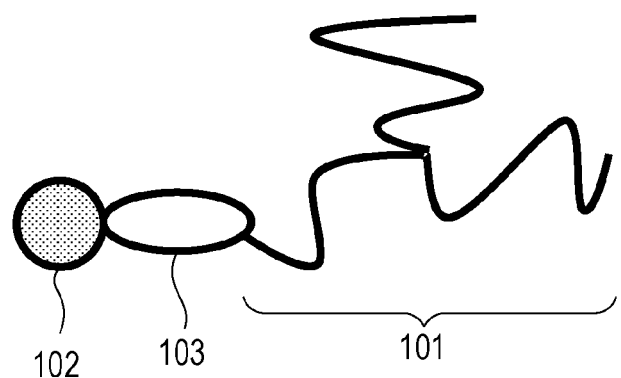
FIG. 1 is a schematic diagram of a compound produced by covalent-bonding of an organic dye which absorbs light in the near-infrared wavelength region and a PEG having a branch.

A compound according to an embodiment of the present invention will be described. The compound according to the present embodiment is characterized in that PEG 102 having a branch and an organic dye 101 which absorbs light in the near-infrared wavelength region (hereafter may be abbreviated to near-infrared organic dye) are covalent-bonded to a linker part 103 which is any one of —NH—, —CO—, —O—, and —S— or which contains at least one of —NH—, —CO—, —O—, and —S—.

The near-infrared organic dye, e.g., ICG, administered to blood adsorbs proteins in the blood and tends to be discharged from a body. The near-infrared organic dye may react with a water molecule in the blood and be decomposed. As a result, even when the near-infrared organic dye is administered to the blood of a living body, the retentivity in blood is low, and the tumor accumulation is low, so that the intensity of photoacoustic signal produced by the tumor is small.

Meanwhile, in the compound according to the present embodiment, the near-infrared organic dye is covalent-bonded to a PEG having a branch and, therefore, the PEG suppresses adsorption of proteins in the blood to the near-infrared organic dye. Consequently, even when the compound according to the present embodiment is administered to the blood of a living body, a property in which the compound is not discharged from the body easily (stealth effect) is obtained. The compound according to aspects of the present invention gains high retentivity in blood and high tumor accumulation on the basis of this stealth effect. In addition, the near-infrared organic dye and the PEG are covalent-bonded, so that water molecules in the blood do not approach the near-infrared organic dye and the near-infrared organic dye is not decomposed easily.

Furthermore, the PEG having a branch, according to the present embodiment, is characterized by being formed from a plurality of PEG units having at least one branched chain structure in the molecule (hereafter may be referred to as branched chain PEG). Examples of features of the branched chain PEG as compared with the single-chain PEG are as described below. The branched chain PEG has low viscosity per molecule of the PEG and, therefore, diffuses easily as compared with the single-chain PEG. Consequently, it is expected that the retentivity in blood and the permeability into a tissue are improved as compared with those of the single-chain PEG. Also, it is expected that the handling in preparation becomes easy because the viscosity is low. The branched chain PEG has a molecular structure in which a PEG unit is bonded to a branch point. Therefore, the molecular motion per PEG molecular weight is limited as compared with the single-chain PEG. As a result, the volume occupied by the molecule becomes relatively small and it is expected that the permeability into a tissue is improved. For such a reason, the compound according to the present embodiment has high retentivity in blood and high tumor accumulation, so that the intensity of photoacoustic signal produced by the tumor is large.

In the compound according to the present embodiment, it is enough that the branched chain PEG and at least one near-infrared organic dye are covalent-bonded to any one of $L^1$ to $L^4$ in the formulae (1) to (6), and a plurality of near-infrared organic dyes may be bonded to a branched chain PEG. In the case where the compound according to the present embodiment includes a branched chain PEG and a plurality of near-infrared organic dyes, it is enough that at least one near-infrared organic dye is covalent-bonded to the branched chain PEG, and the other near-infrared organic dyes may be noncovalent-bonded. Likewise, in the case where a near-infrared organic dye and a plurality of branched chain PEGs are included, it is enough that at least one branched chain PEG is covalent-bonded to the near-infrared organic dye, and the other branched chain PEGs may be noncovalent-bonded. Meanwhile, $L^1$ to $L^4$ may independently be a linker part containing at least one of —NH—, —CO—, —O—, and —S—. Here, the linker part refers to a part having a function to bond the branched chain PEG to the near-infrared organic dye. Examples include bifunctional compounds, e.g., 1,6-bismaleimidohexane and succinimidyl trans-4-(N-maleimidylmethyl)-cyclohexane-1-carboxylate. Other examples may include alkyl groups containing a carbonyl group, an amide group, an ester group, a piperazyl group, or the like. In other examples, polypeptides having any chain length may be used, and the polypeptides may be capture molecules described later. The polypeptide may form a covalent bond by using any one of a carbonyl group, an amino group, and a thiol group in the chain. For example, a N-PEG maleimide group and a thiol group may form a maleimide-thiol bond under a neutral condition at room temperature.

The compound according to the present embodiment may include a capture molecule which is specifically bonded to a target part.

The compound according to the present embodiment is specifically characterized in that the compound is represented by any one of the following formulae (1) to (6).

[Chem. 14]

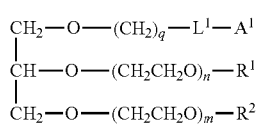

(1)

[Chem. 15]

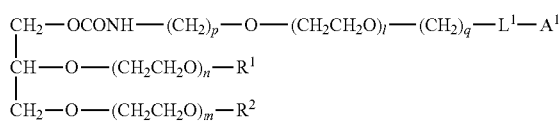

(2)

[Chem. 16]

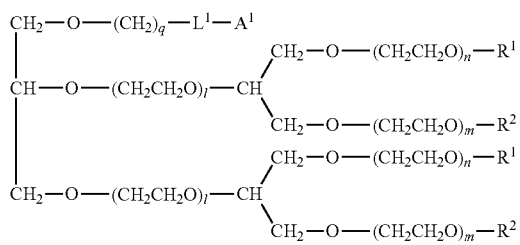

(3)

[Chem. 17]

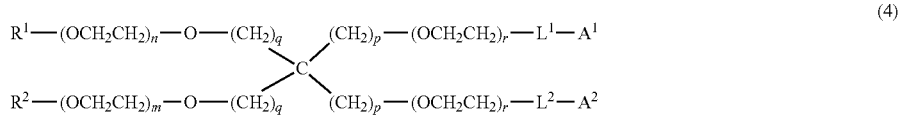

(4)

[Chem. 18]

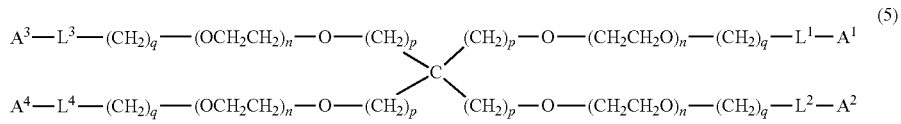

(5)

[Chem. 19]

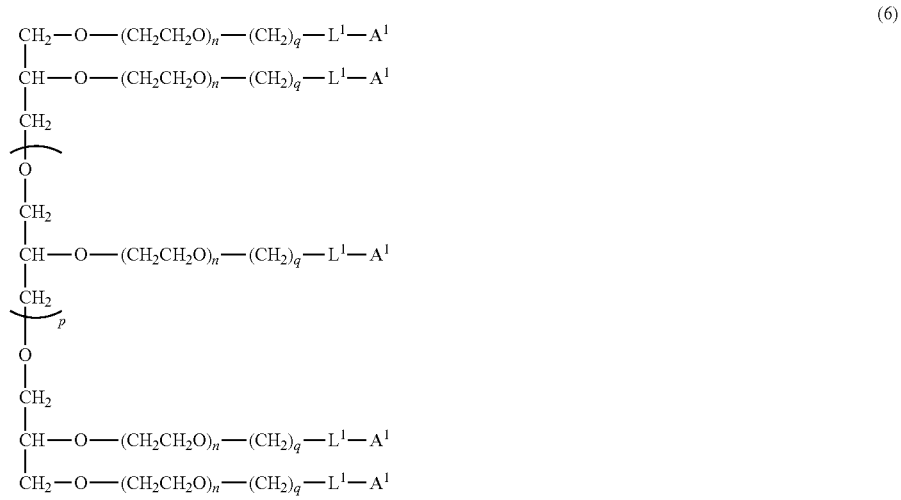

(6)

In the above-described formula (1), $A^1$ represents an organic dye which absorbs light in the near-infrared wavelength region, $L^1$ represents a linker part which is any one of —NH—, —CO—, —O—, and —S— or which contains at least one of —NH—, —CO—, —O—, and —S—, q represents an integer of 1 to 5, m and n represent independently an integer of 10 or more and 2,500 or less, and $R^1$ and $R^2$ represent independently an alkyl group having the carbon number of 1 to 5.

In the formula (2), $A^1$ represents an organic dye which absorbs light in the near-infrared wavelength region, $L^1$ represents a linker part which is any one of —NH—, —CO—, —O—, and —S— or which contains at least one of —NH—, —CO—, —O—, and —S—, p and q represent independently an integer of 1 to 5, l, m, and n represent independently an integer of 10 or more and 2,500 or less, and $R^1$ and $R^2$ represent independently an alkyl group having the carbon number of 1 to 5.

In the formula (3), $A^1$ represents an organic dye which absorbs light in the near-infrared wavelength region, $L^1$ represents a linker part which is any one of —NH—, —CO—, —O—, and —S— or which contains at least one of —NH—, —CO—, —O—, and —S—, q represents an integer of 1 to 5, l, m, and n represent independently an integer of 10 or more and 2,500 or less, and $R^1$ and $R^2$ represent independently an alkyl group having the carbon number of 1 to 5.

In the formula (4), $A^1$ and $A^2$ represent independently an organic dye which absorbs light in the near-infrared wavelength region, $L^1$ and $L^2$ represent independently a linker part which is any one of —NH—, —CO—, —O—, and —S— or which contains at least one of —NH—, —CO—, —O—, and —S—, p, q, and r represent independently an integer of 1 to 5, m and n represent independently an integer of 10 or more and 2,500 or less, and $R^1$ and $R^2$ represent independently an alkyl group having the carbon number of 1 to 5.

In the formula (5), $A^1$, $A^2$, $A^3$, and $A^4$ represent independently an organic dye which absorbs light in the near-infrared wavelength region, $L^1$, $L^2$, $L^3$, and $L^4$ represent independently a linker part which is any one of —NH—, —CO—, —O—, and —S— or which contains at least one of —NH—, —CO—, —O—, and —S—, p and q represent independently an integer of 1 to 5, and n represents an integer of 10 or more and 2,500 or less.

In the formula (6), $A^1$ represents an organic dye which absorbs light in the near-infrared wavelength region, $L^1$ represents a linker part which is any one of —NH—, —CO—, —O—, and —S— or which contains at least one of —NH—, —CO—, —O—, and —S—, p and q represent independently an integer of 1 to 5, and n represents an integer of 10 or more and 2,500 or less.

In the above-described formulae (1) to (6), $A^1$, $A^2$, $A^3$, and $A^4$ can independently be represented by any one of the following formula (7) or formula (8).

[Chem. 20]

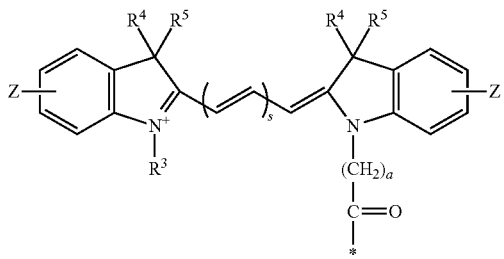

(7)

[Chem. 21]

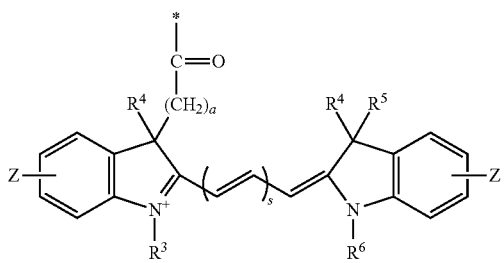

(8)

In the above-described formula (7) and formula (8), the symbol * is bonded to any one of $L^1$, $L^2$, $L^3$, and $L^4$ in the above-described formulae (1) to (6).

In this regard, in the present specification, the symbol * represents the following mark in the structural formula.

[Chem.22]

*

In the above-described formula (7) and formula (8), Z forms a cyclic aromatic ring composed of a benz[e]indole ring, benz[f]indole ring, or benz[g]indole ring together with a hydrogen atom, a sulfonate group, or an indole ring bonded to Z, and furthermore, a hydrogen atom of the cyclic aromatic ring may be substituted with an alkyl group having the carbon number of 1 to 10, an alkoxy group having the carbon number of 1 to 10, or a sulfonate group.

In the above-described formula (7) and formula (8), $R^3$ represents any one of an alkyl group having the carbon number of 1 to 10 and —$(CH_2)_b$—$SO_3^-$ (b represents an integer of 1 to 10), and in the case where $R^3$ is an alkyl group, a halogen ion or an organic acid ion may be contained as a counter ion.

$R^4$ and $R^5$ represent independently any one of a hydrogen atom, an alkyl group having the carbon number of 1 to 10, an alkoxy group having the carbon number of 1 to 10, —$(CH_2)_b$—$SO_3^-$ (b represents an integer of 1 to 10), and —$(CH_2)_b$—$SO_3X$ (b represents an integer of 1 to 10 and X represents any one of sodium, potassium, ammonium, triethylammonium, lysine, and arginine).

In the above-described formula (7) and formula (8), a represents an integer of 1 to 10 and s represents 2 or 3.

In the above-described formula (8), $R^6$ represents any one of an alkyl group having the carbon number of 1 to 10, —$(CH_2)_b$—$SO_3^-$ (b represents an integer of 1 to 10), and —$(CH_2)_b$—$SO_3X$ (b represents an integer of 1 to 10 and X represents any one of sodium, potassium, ammonium, triethylammonium, lysine, and arginine).

In the present embodiment, a in the formula (7) can be an integer of 2 to 6, and b in $R^3$, $R^4$, and $R^5$ in the formula (7) can be an integer of 2 to 6.

In the present embodiment, a in the formula (8) can be an integer of 2 to 6, and b in $R^3$, $R^4$, and $R^5$ in the formula (8) can be an integer of 2 to 6.

In the case where the above-described a and b are 6 or less, the hydrophobicity does not become high and, therefore, nonspecific adsorption does not occur in a living body easily.

In the present embodiment, the above-described formula (7) can be represented by any one of the following formulae (21) to (26).

[Chem. 23]

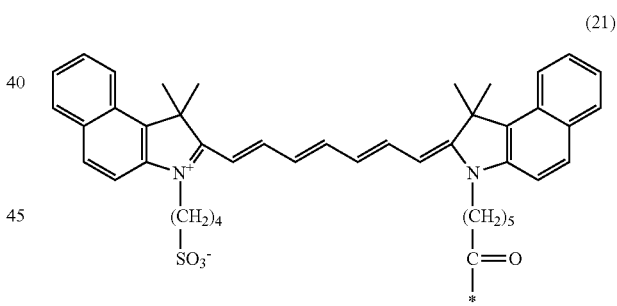

(21)

[Chem. 24]

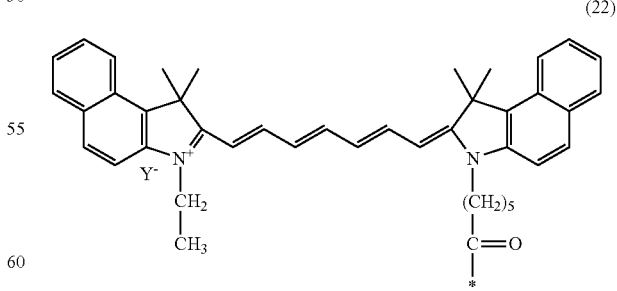

(22)

In the formula (22), $Y^-$ represents any one of a halogen ion, e.g., a chloride ion, a bromide ion, or an iodide ion, or an organic acid ion, e.g., an acetate ion, a tartrate ion, or a succinate ion.

[Chem. 25]
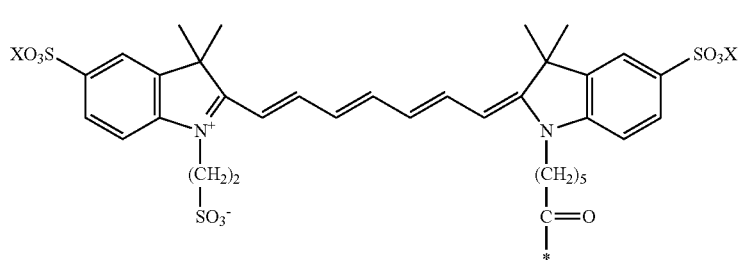
(23)
[Chem. 26]
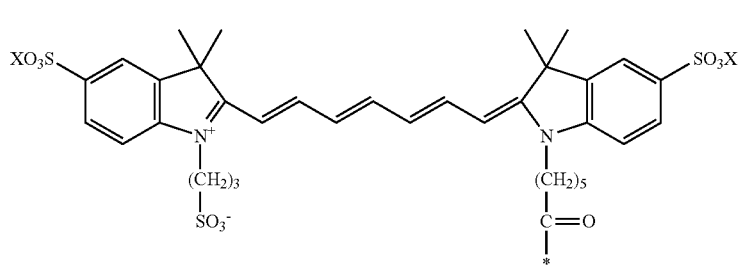
(24)
[Chem. 27]
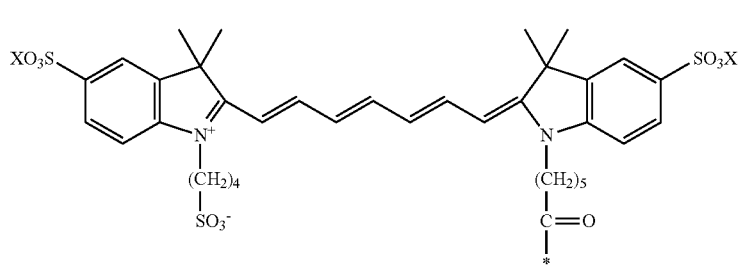
(25)
[Chem. 28]
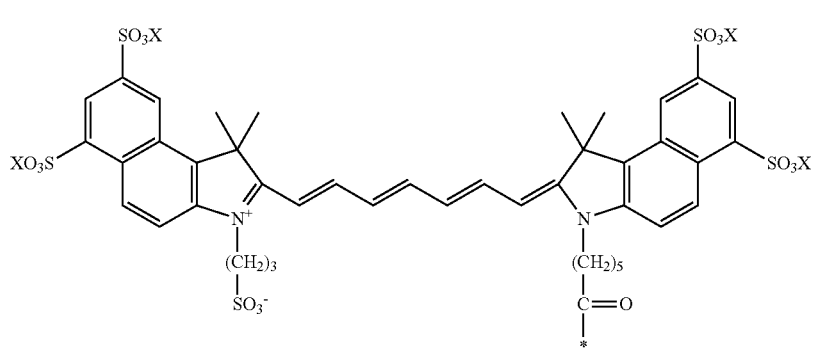
(26)

In the above-described formulae (23) to (26), X represents any one of sodium, potassium, ammonium, triethylammonium, lysine, and arginine.

In the present embodiment, the above-described formula (8) can be represented by any one of the following formulae (27) and (28).

[Chem. 29]

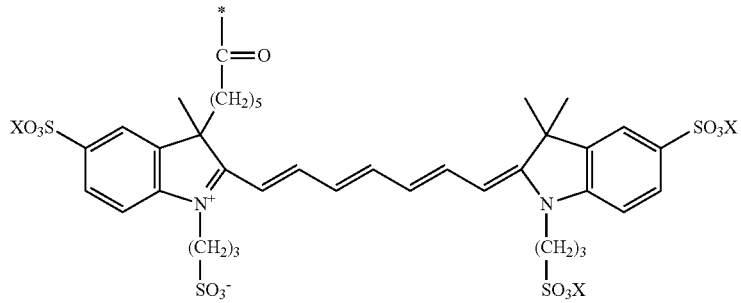

(27)

[Chem. 30]

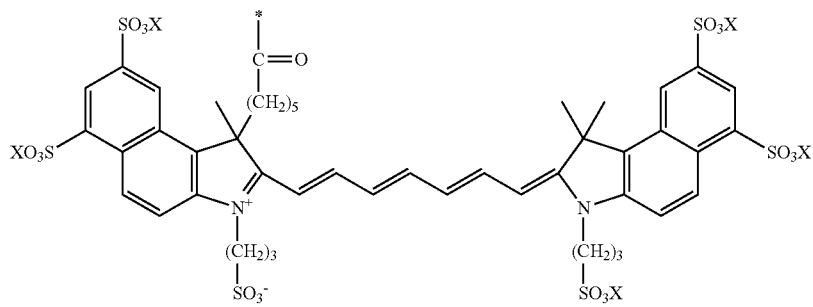

(28)

In the above-described formulae (27) and (28), X represents any one of sodium, potassium, ammonium, triethylammonium, lysine, and arginine.

In the formulae (1) to (6), at least one linker part of $L^1$ to $L^4$ may be a polypeptide or a single-chain antibody.

In the formulae (1) to (6), at least one of $L^1$ to $L^4$ is represented by the following formula (46),

[Chem. 54]

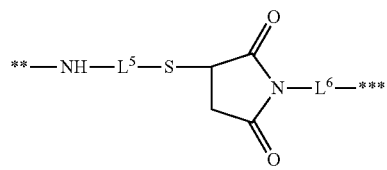

(46)

where $L^5$ represents a polypeptide or a single-chain antibody, —NH— represents a bond through an amino group of an amino acid in the polypeptide or the single-chain antibody, —S— represents a bond through a thiol group of an amino acid in the polypeptide or the single-chain antibody, $L^6$ represents an alkyl chain having the carbon number of 1 to 10 and including a carbonyl group, an amide group, an ester group, a piperazyl group, or the like, the symbol  is bonded to at least one of $A^1$ to $A^4$, and the symbol * is bonded to the alkyl chain side or the ethylene glycol chain side of the formulae (1) to (6).

In the formula (46), $L^6$ is —$(CH_2)_2$—C(=O)—NH—, where the ethylene group side is bonded to a nitrogen atom of a maleimide group and the amide group side is bonded to the symbol ***.

PEG Having Branch

The PEG having a branch according to the present embodiment is a water-soluble polymer and exerts effects of increasing a serum half-life of protein, reducing the immunogenicity, and the like. The molecular weight of the PEG is preferably within the range of 400 or more and 100,000 or less, and further preferably 20,000 or more. It is believed that if the molecular weight is 20,000 or more, a larger amount of PEG can be accumulated in a tumor part as compared with a normal part in a living body on the basis of an enhanced permeability and retention (EPR) effect. If the molecular weight is 20,000 or more, excretion from a kidney is suppressed and, therefore, it is expected that the retentivity in blood increases as compared with a low-molecular weight PEG. As the molecular weight of PEG increases, the viscosity of the solution increases, so that the molecular weight of PEG is preferably 100,000 or less.

In the present embodiment, a PEG having at least one reactive functional group, which is able to be covalent-bonded to the near-infrared organic dye, per PEG molecule can be used. The reactive functional group may be selected appropriately in accordance with the functional group included in the dye to be bonded. Examples of reactive functional groups can include an amino group, a hydroxyl group, a thiol group, a carbonyl group, a sulfhydryl group, an epoxy group, a glycidyl group, a N-succinimidyloxy group, a N-sulfosuccinimidyloxy group, and a N-maleimidoalkyl group.

The PEG which reacts with the near-infrared organic dye and which has a branch can be represented by any one of the following formulae (9) to (14).

In the above-described formula (9), $L^1$ includes at least one of $-NH_2$, $-COOH$, $-OH$, $-SH$, a sulfhydryl group, an epoxy group, a glycidyl group, a N-succinimidyloxy group, a N-sulfosuccinimidyloxy group, and a N-maleimidoalkyl group, q represents an integer of 1 to 5, m and n represent independently an integer of 10 or more and 2,500

[Chem. 31]

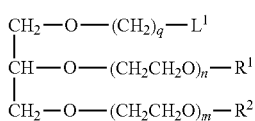

(9)

[Chem. 32]

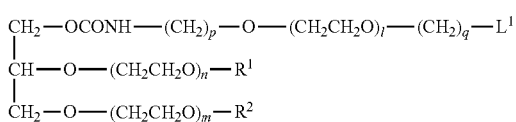

(10)

[Chem. 33]

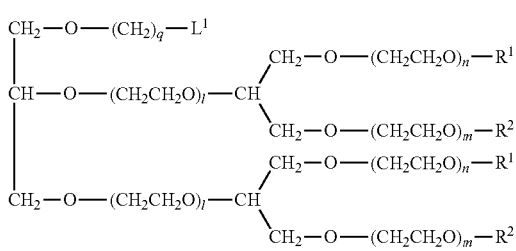

(11)

[Chem. 34]

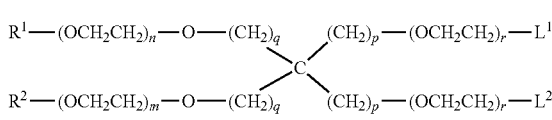

(12)

[Chem. 35]

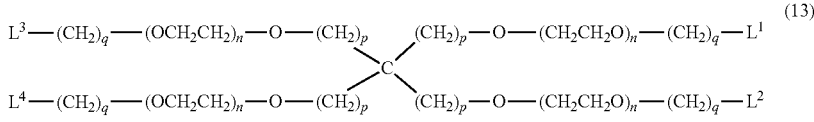

(13)

[Chem. 36]

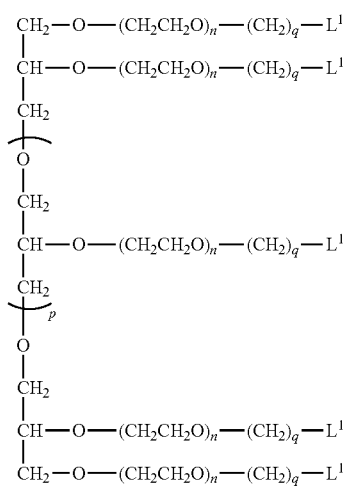

(14)

or less, and $R^1$ and $R^2$ represent independently an alkyl group having the carbon number of 1 to 5.

In the above-described formula (10), $L^1$ includes at least one of —$NH_2$, —COOH, —OH, —SH, a sulfhydryl group, an epoxy group, a glycidyl group, a N-succinimidyloxy group, a N-sulfosuccinimidyloxy group, and a N-maleimidoalkyl group, p and q represent independently an integer of 1 to 5, l, m, and n represent independently an integer of 10 or more and 2,500 or less, and $R^1$ and $R^2$ represent independently an alkyl group having the carbon number of 1 to 5.

In the above-described formula (11), $L^1$ includes at least one of —$NH_2$, —COOH, —OH, —SH, a sulfhydryl group, an epoxy group, a glycidyl group, a N-succinimidyloxy group, a N-sulfosuccinimidyloxy group, and a N-maleimidoalkyl group, q represents an integer of 1 to 5, l, m, and n represent independently an integer of 10 or more and 2,500 or less, and $R^1$ and $R^2$ represent independently an alkyl group having the carbon number of 1 to 5.

In the above-described formula (12), $L^1$ and $L^2$ include independently at least one of —$NH_2$, —COOH, —OH, —SH, a sulfhydryl group, an epoxy group, a glycidyl group, a N-succinimidyloxy group, a N-sulfosuccinimidyloxy group, and a N-maleimidoalkyl group, p, q, and r represent independently an integer of 1 to 5, m and n represent independently an integer of 10 or more and 2,500 or less, and $R^1$ and $R^2$ represent independently an alkyl group having the carbon number of 1 to 5.

In the above-described formula (13), $L^1$, $L^2$, $L^3$, and $L^4$ include independently at least one of —$NH_2$, —COOH, —OH, —SH, a sulfhydryl group, an epoxy group, a glycidyl group, a N-succinimidyloxy group, a N-sulfosuccinimidyloxy group, and a N-maleimidoalkyl group, p and q represent independently an integer of 1 to 5, and n represents an integer of 10 or more and 2,500 or less.

In the above-described formula (14), $L^1$ includes at least one of —$NH_2$, —COOH, —OH, —SH, a sulfhydryl group, an epoxy group, a glycidyl group, a N-succinimidyloxy group, a N-sulfosuccinimidyloxy group, and a N-maleimidoalkyl group, p and q represent independently an integer of 1 to 5, and n represents an integer of 10 or more and 2,500 or less.

Examples of the PEG, which reacts with the near-infrared organic dye and which has a branch, according to the present embodiment, include compounds represented by any one of the following formulae (15) to (20) and (40).

[Chem. 37]

(15)

[Chem. 38]

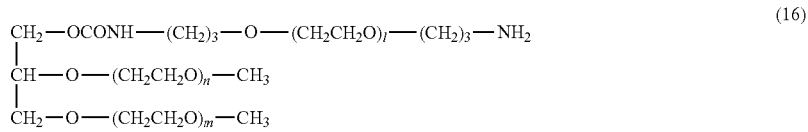

(16)

[Chem. 39]

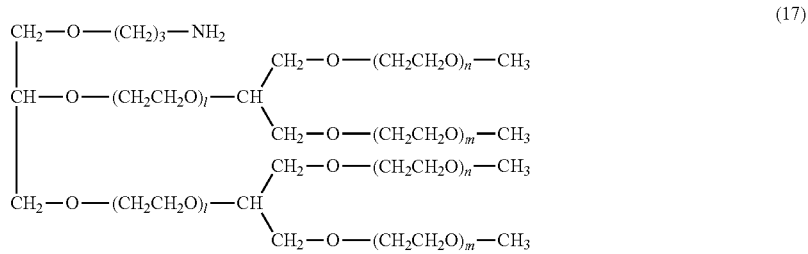

(17)

[Chem. 40]

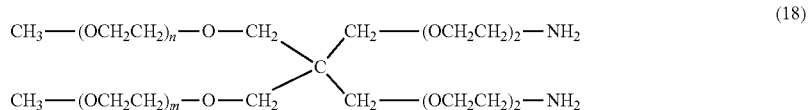

(18)

[Chem. 41]

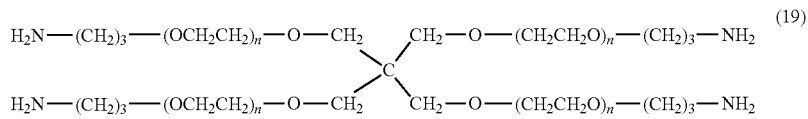

(19)

[Chem. 42]

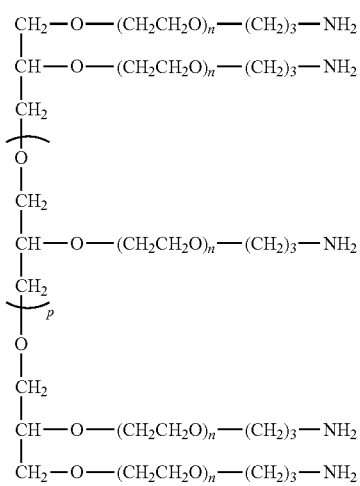

(20)

[Chem. 54]

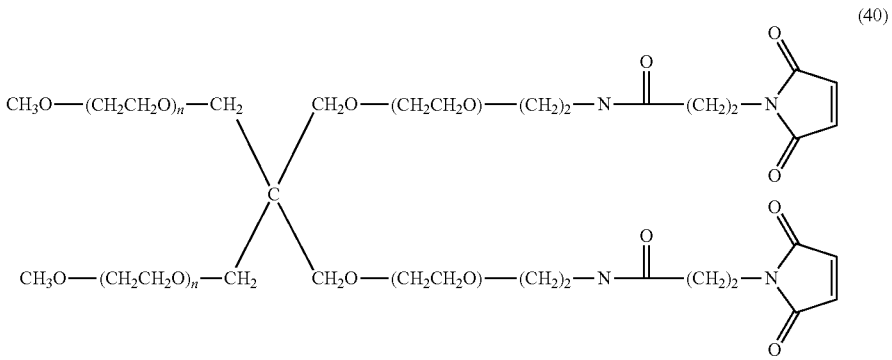

(40)

As for the compounds having molecular weights of 20,000, 40,000, and 60,000 among the compounds represented by the above-described formula (15), SUNBRIGHT GL2-200PA (produced by NOF CORPORATION), SUNBRIGHT GL2-400PA (produced by NOF CORPORATION), and SUNBRIGHT GL2-600PA (produced by NOF CORPORATION), respectively, are mentioned.

As for the compound having a molecular weight of 50,000 among the compounds represented by the above-described formula (16), SUNBRIGHT GL3-400PA 100U (produced by NOF CORPORATION) is mentioned.

As for the compounds having molecular weights of 60,000 and 80,000 among the compounds represented by the above-described formula (17), SUNBRIGHT GL4-600PA (produced by NOF CORPORATION) and SUNBRIGHT GL4-800PA (produced by NOF CORPORATION), respectively, are mentioned.

As for the compound having a molecular weight of 40,000 among the compounds represented by the above-described formula (18), SUNBRIGHT PTE-400EA (produced by NOF CORPORATION) is mentioned.

As for the compound having a molecular weight of 40,000 among the compounds represented by the above-described formula (19), SUNBRIGHT PTE-400PA (produced by NOF CORPORATION) is mentioned.

As for the compounds having molecular weights of 15,000 and 40,000 among the compounds represented by the above-described formula (20), SUNBRIGHT HGEO-150PA (produced by NOF CORPORATION) and SUNBRIGHT HGEO-400PA (produced by NOF CORPORATION), respectively, are mentioned.

As for the compounds having molecular weights of 20,000 and 40,000 among the compounds represented by the above-described formula (40), SUNBRIGHT PTE2-200MA2 (produced by NOF CORPORATION) and SUNBRIGHT PTE-400MA2 (produced by NOF CORPORATION), respectively, are mentioned.

Near-Infrared Organic Dye

In the present embodiment, the near-infrared organic dye is not specifically limited insofar as the dye absorbs light in the near-infrared wavelength region and produces an acoustic wave. In this regard, the near-infrared wavelength region refers to a region of 600 nm or more and 1,300 nm or less.

In the present embodiment, examples of near-infrared organic dyes may include azine based dyes, acridine based dyes, triphenylmethane based dyes, xanthene based dyes, porphyrin based dyes, cyanine based dyes, phthalocyanine based dyes, styryl based dyes, pyrylium based dyes, azo based dyes, quinone based dyes, tetracycline based dyes, flavone based dyes, polyene based dyes, BODIPY (registered trademark) based dyes, and indigoid based dyes.

Examples of the above-described cyanine based dyes may include Indocyanine Green (ICG), Alexa Fluor (registered trademark) based dyes, e.g., Alexa 750, (produced by Invitrogen Corporation), Cy (registered trademark) based dyes (produced by GE Healthcare Bio-Sciences KK), IR-783, IR-806, IR-820 (produced by Sigma-Aldrich Japan K.K.), IRDye 800CW, IRDye 800RS (registered trademark) (produced by LI-COR, Inc.), ADS780WS, ADS795WS, ADS830WS, and ADS832WS (produced by American Dye Source, Inc.).

In the present embodiment, the structure of the near-infrared organic dye which reacts with the PEG having a branch is represented by the following formula (29).

[Chem.43]

B-B'  (29)

In the formula (29), B is represented by the above-described formula (7) or formula (8).

In the formula (29), B' is represented by any one of the following formulae (30) to (33).

[Chem. 44]

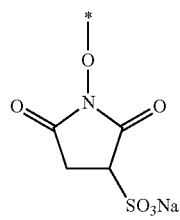

(30)

[Chem. 45]

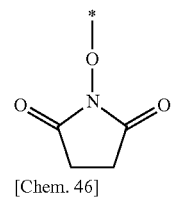

(31)

[Chem. 46]

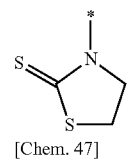

(32)

[Chem. 47]

*—OH  (33)

An example of the above-described formula (29) can be any one of the compound represented by the following formula (34) (ICG-sulfo-OSu (produced by Dojindo Laboratories, registered trademark)), the compound represented by the following formula (35), the compound represented by the following formula (36), the compound represented by the following formula (37), the compound represented by the following formula (38), and the compound represented by the following formula (39).

[Chem. 48]

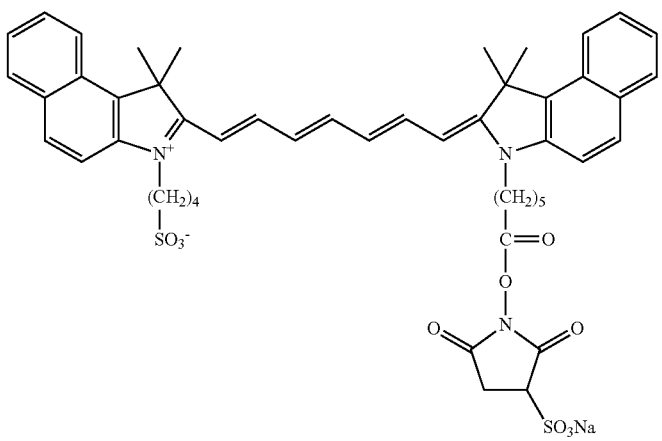

(34)

[Chem. 49]

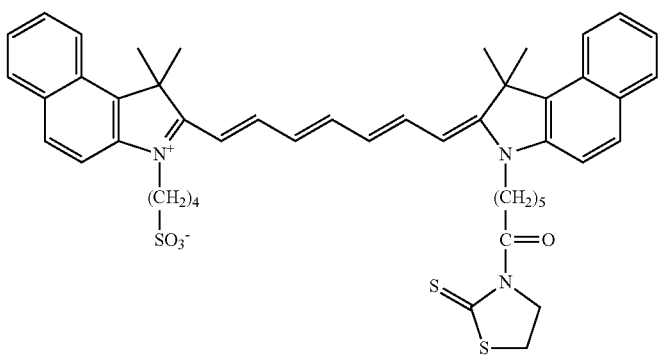

(35)

[Chem. 50]
(36)
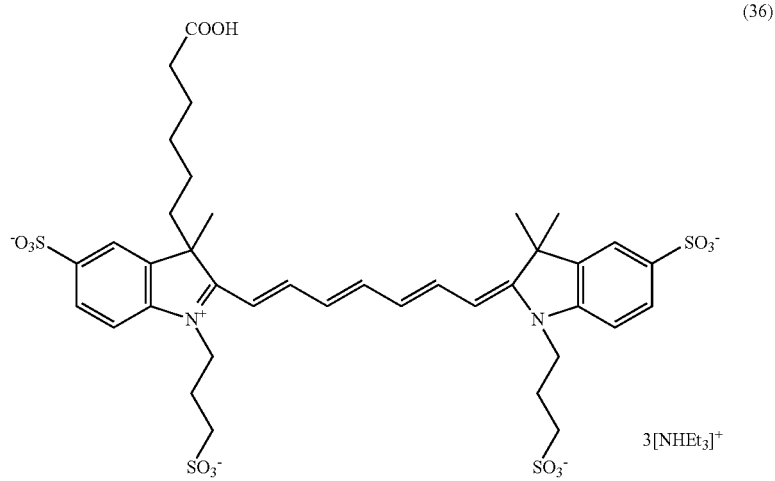
[Chem. 51]
(37)
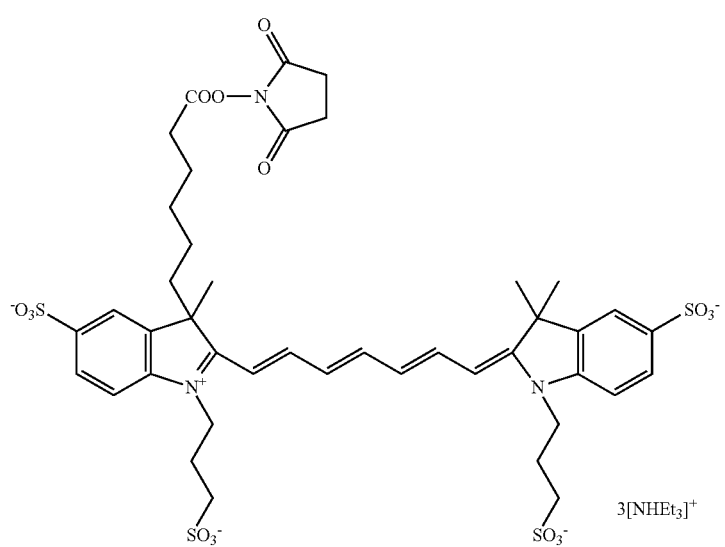
[Chem. 52]
(38)
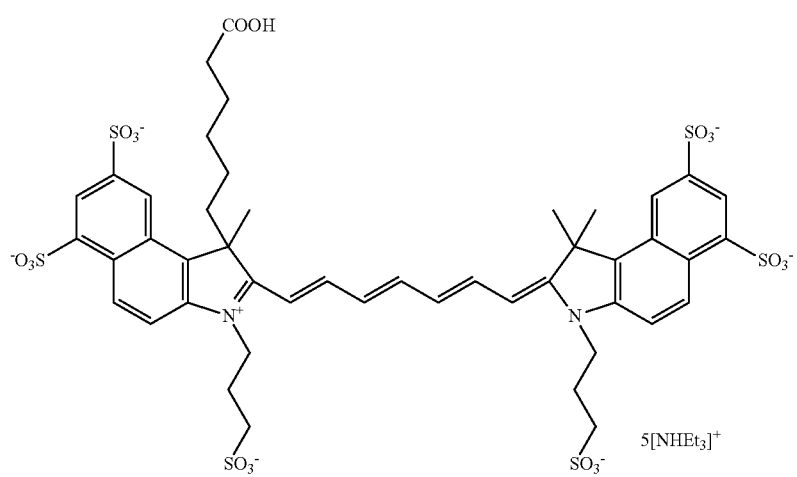

[Chem. 53]

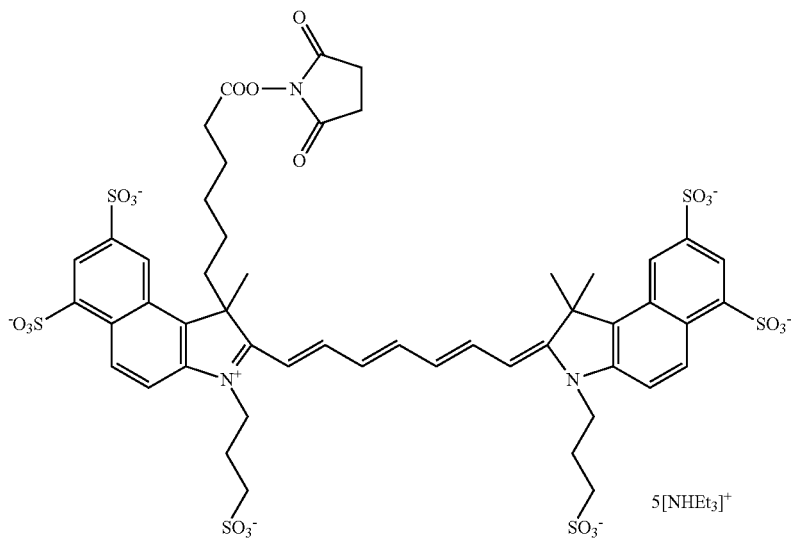

(39)

Method for Preparing Compound

In the present embodiment, the compound is prepared by bonding the PEG having a branch to the near-infrared organic dye through at least one of an amino group, a thiol group, a carboxyl group, a hydroxyl group, a sulfhydryl group, an epoxy group, a glycidyl group, a N-succinimidyloxy group, a N-sulfosuccinimidyloxy group, and a N-maleimidoalkyl group by a known coupling reaction. In particular, bonding through an amino group can be performed. An amino group is allowed to be present at a terminal or the like of the PEG having a branch, and a reaction is induced in a weak alkaline pH region efficiently and selectively. The near-infrared organic dye bonded to the PEG having a branch by the above-described reaction may be washed and refined by a known protein refining method, e.g., an ultrafiltration method or size exclusion column chromatography.

As for the bonding between the PEG having a branch and the near-infrared organic dye, at least one of the above-described amino group, thiol group, carboxyl group, hydroxyl group, sulfhydryl group, epoxy group, glycidyl group, N-succinimidyloxy group, N-sulfosuccinimidyloxy group, and N-maleimidoalkyl group may be bonded directly to a derivative of the near-infrared organic dye, or the PEG may be bonded to the near-infrared organic dye through various cross-linking agents (cross-linkers).

Addition Agent

The contrast medium for photoacoustic imaging according to the present embodiment may contain an addition agent used in freeze-drying. Examples of addition agents include glucose, lactose, mannitol, polyethylene glycol, glycine, sodium chloride, and sodium hydrogen phosphate. One type of addition agent may be used alone or some types may be used in combination.

Photoacoustic Imaging Contrast Medium

The photoacoustic imaging (hereafter may be abbreviated to PAI) contrast medium according to the present embodiment includes the above-described compound and a dispersion medium. In this regard, PAI is a concept containing photoacoustic tomography. Examples of dispersion media include physiological saline, distilled water for injection, phosphate buffered saline, and glucose aqueous solution.

The PAI contrast medium according to the present embodiment may contain pharmacologically allowable additives, for example, a vasodilator, as necessary.

The PAI contrast medium according to the present embodiment may be dispersed in the above-described dispersion medium in advance, or be made into a kit so as to be used by being dispersed into the dispersion medium before administration to a living body.

A larger amount of PAI contrast medium according to the present embodiment may be accumulated in a tumor part as compared with a normal part in a living body taking advantage of the EPR effect, when being administered to the living body. As a result, when particles are administered to the living body and, thereafter, light is applied to the living body to detect an acoustic wave from the living body, an acoustic wave produced by a tumor part is allowed to become larger than an acoustic wave produced by a normal part. Consequently, the PAI contrast medium according to the present embodiment can be used for imaging of a tumor.

The PAI contrast medium according to the present embodiment may also be used for imaging of a lymph node and, in particular, can be used as a contrast medium of a sentinel lymph node (hereafter may be abbreviated to SLN). This is because the size is large as compared with a single dye and, thereby, retention in the sentinel lymph node occurs easily, so that an improvement in accumulation is expected.

Capture Molecule

The capture molecule in the present embodiment refers to, for example, a substance specifically bonded to a target part, e.g., a tumor, or a substance specifically bonded to a substance present around a target part, and may be selected optionally from, for example, living body molecules and chemical substances, e.g., drugs. Specific examples include antibodies, antibody fragments, artificial antibodies, e.g., single-chain antibodies, enzymes, biologically active peptides, glycopeptides, saccharides, lipids, and molecular recognition compounds. These substances may be used alone or a plurality of them may be used in combination. In the case where a compound chemically bonded to the capture molecule is used, specific detection of a target part and tracing of dynamic behavior, localization, drug efficacy, metabolism, and the like of the target substance may be performed.

Photoacoustic Imaging Method

A method for detecting the compound, according to the present embodiment, administered to a living body by using a photoacoustic imaging apparatus will be described. The method for detecting the compound according to the present embodiment includes the following steps (a) and (b).

(a) A step to apply light in a wavelength region of 600 nm to 1,300 nm to a specimen which has been administered the compound according to the present embodiment (b) A step to detect an acoustic wave produced by the above-described compound present in the inside of the above-described specimen In addition, the compound according to the present embodiment may include a step to reconfigure the spatial photoacoustic signal intensity distribution on the basis of the wavelength, phase, time information, and the like of the acoustic wave obtained in the above-described step (b). In this regard, a three-dimensional image reconfiguration may be performed on the basis of the wavelength, phase, and time information of the photoacoustic signal obtained in the above-described step (b). The data obtained by the image reconfiguration may take on any form insofar as the positional information of the intensity distribution of the photoacoustic signal is grasped. For example, the photoacoustic signal intensity may be expressed in a three-dimensional space or the photoacoustic signal intensity may be expressed on a two-dimensional plane. It is also possible that pieces of information is acquired from the same observation subject by different imaging methods and the relationship in positional correspondence between those pieces of information and the photoacoustic intensity distribution is acquired.

In the above-described step (a), a specimen which has been administered the compound according to the present embodiment by a method of oral administration, injection, or the like may be used.

In the above-described step (b), the apparatus to emit light to be applied to the specimen and the apparatus to detect the photoacoustic signal produced by the compound according to the present embodiment are not specifically limited.

The light source to apply the light to the specimen in the above-described step (b) is not specifically limited insofar as laser pulse light with at least one wavelength selected from the range of 600 nm to 1,300 nm is applied to the above-described specimen. Examples of apparatuses to apply the laser pulse light include a titanium sapphire laser (LT-2211-PC, produced by Lotis), OPO laser (LT-2214 OPO, produced by Lotis), and an alexandrite laser.

The apparatus to detect an acoustic wave is not specifically limited and various apparatuses may be used. For example, a commercially available photoacoustic imaging apparatus (Nexus128, produced by Endra Inc.) may be employed.

The imaging method by using the compound according to the present embodiment may perform imaging of a predetermined part, e.g., a tumor, a lymph node, or a blood vessel, through the above-described steps (a) and (b).

EXAMPLES

The present invention will be described below in further detail with reference to examples, although the present invention is not limited to these examples. In this regard, hereafter Mw represents a molecular weight.

Method for Measuring Photoacoustic Signal Intensity

In the examples according to the present invention, the photoacoustic signal intensity was measured as described below.

Photoacoustic signals were measured before a prepared compound was administered and at any given timing after administration by using the commercially available photoacoustic imaging apparatus (Nexus128, produced by Endra Inc.), so that three-dimensional reconfiguration data were obtained respectively. The photoacoustic intensity in a region of interest (ROI) was measured on the basis of the resulting three-dimensional reconfiguration data.

Evaluation Example of Amount of Migration to Tumor Mass

In the example according to the present invention, the amount of migration of the compound to a tumor mass was evaluated using a tumor-bearing model mouse. The tumor-bearing mouse was prepared by subcutaneously transplanting a mouse colon cancer cell line (Colon 26) into a nude mouse. A contrast medium was administered to the tumor-bearing mouse and photoacoustic imaging was performed. In addition, fluorescent imaging of a tumor-bearing mouse was performed one day after administration as a comparative example. The fluorescent imaging was performed using IVIS (registered trademark) Imaging System and fluorescent intensity of a region of interest (ROI) of the tumor portion was measured.

Evaluation of Tumor Accumulation of Contrast Medium

The tumor accumulation was evaluated by an intravenous injection of 100 microliters (13 nmol in terms of ICG) of various ICG-PEG aqueous solution into tumor-bearing mouse models, in which various cells were subcutaneously transplanted into BALB/c Slc-nu/nu mice. The mice were euthanized with a carbon dioxide gas 24 hours after the administration. Subsequently, each cancer tissue was enucleated. The cancer tissue was transferred to a plastic tube, 1% Triton-X100 aqueous solution 1.25 times the cancer tissue in weight was added, and a homogenate was produced using a plastic pestle. Thereafter, DMSO 20.25 times the cancer tissue in weight was added, so as to prepare a solution of dye extracted from the tumor tissue. The ICG-PEG solution having a known concentration was diluted to various concentrations with a Triton-X100 solution containing the above-described cancer tissue. A standard solution for calibration was prepared by adding DMSO 20.25 times the resulting diluted solution in amount. The amount of dye in the cancer tissue (% ID/g) was quantified by using IVIS (registered trademark) Imaging System 200 Series (produced by Caliper Life Science Inc.) and measuring the fluorescent intensity of the solution of the dye extracted from the tumor tissue and the standard solution for calibration in the state of the plastic tube.

Example 1

Preparation of Compound Through Covalent-Bonding of Near-Infrared Organic Dye and PEG Having Branch As for the near-infrared organic dye, ICG-sulfo-OSu (Dojindo Laboratories, code: I254, compound represented by the above-described formula (34)) was used, and 1 mg (1.25 micromoles) of ICG-sulfo-OSu was dissolved into 100 microliters of DMSO. Meanwhile, various PEGs were weighed into 1.5-mL plastic tubes. PEG was dissolved by 50 mM carbonate buffer (pH 9.0), so that the $NH_2$ concentration was specified to be 0.625 mM (Table 1).

The branched chain PEGs used in the present embodiment were monoamine branched chain SUNBRIGHT GL2-200PA (produced by NOF CORPORATION, Mw 20,000), monoamine branched chain SUNBRIGHT GL2-400PA (produced by NOF CORPORATION, Mw 40,000), monoamine branched chain SUNBRIGHT GL2-600PA (produced by NOF CORPORATION, Mw 60,000), monoamine branched chain SUNBRIGHT GL3-400PA 100U (produced by NOF CORPORATION, Mw 50,000), monoamine branched chain SUNBRIGHT GL4-600PA (produced by NOF CORPORATION, Mw 60,000), monoamine branched chain SUNBRIGHT GL4-800PA (produced by NOF CORPORATION, Mw 80,000), diamine branched chain SUNBRIGHT PTE2-400EA (produced by NOF CORPORATION, Mw 40,000), tetramine branched chain SUNBRIGHT PTE-400PA (produced by NOF CORPORATION, Mw 40,000), octamine branched chain SUNBRIGHT HGEO-150PA (produced by NOF CORPORATION, Mw 15,000), and octamine branched chain SUNBRIGHT HGEO-400PA (produced by NOF CORPORATION, Mw 40,000).

Combinations of the monoamine branched chain PEG, the diamine branched chain PEG, the tetramine branched chain PEG, or the octamine branched chain PEG and ICG-sulfo-OSu are shown in Table 2. The combination of a tricarbocyanine dye and a PEG may be referred to as a contrast medium in the present specification. Meanwhile, ICG-Gly was also synthesized by reacting ICG-sulfo-OSu with glycine at a molar ratio of 10, so as to serve as a reference sample (Table 2). The typical structure of each of the samples, MB2_20 k-ICG, MB2_40 k-ICG, and MB2_60 k-ICG, which are prepared in the present example, is represented by the formula (40) and the molecular weights are 20 k, 40 k, and 60 k, respectively. The structure of MB3_30 k-ICG is represented by the formula (41) and the molecular weight is 50 k. The structure of MB4_60 k-ICG and MB4_80 k-ICG are represented by the formula (42) and the molecular weights are 60 k and 80 k, respectively. The structure of DB_40 k-ICG2 is represented by the formula (43) (in the formula, q=3) and the molecular weight is 40 k. The structure of TB_40 k-ICG4 is represented by the formula (44) (in the formula, q=3) and the molecular weight is 40 k. The structure of OB_15 k-ICG8 and OB_40 k-ICG8 are represented by the formula (45) (in the formula, q=3) and the molecular weights are 15 k and 40 k, respectively.

TABLE 1

| Product name of PEG employed | Molecular weight | The number of $NH_2$ per PEG | PEG weight (mg) | Amount of $NH_2$ (micromoles) | Carbonate buffer (microliters) | $NH_2$ concentration (mM) |
| --- | --- | --- | --- | --- | --- | --- |
| SUNBRIGHT GL2-200PA | 20000 | 1 | 10 | 0.25 | 400 | 1.25 |
| SUNBRIGHT GL2-400PA | 40000 | 1 | 20 | 0.25 | 400 | 1.25 |
| SUNBRIGHT GL2-600PA | 60000 | 1 | 30 | 0.25 | 400 | 1.25 |
| SUNBRIGHT GL3-400PA 100U | 50000 | 1 | 25 | 0.25 | 400 | 1.25 |
| SUNBRIGHT GL4-600PA | 60000 | 1 | 30 | 0.25 | 400 | 1.25 |
| SUNBRIGHT GL4-800PA | 80000 | 1 | 40 | 0.25 | 400 | 1.25 |
| SUNBRIGHT PTE2-400EA | 40000 | 2 | 10 | 0.25 | 400 | 1.25 |
| SUNBRIGHT PTE-400PA | 40000 | 4 | 5 | 0.25 | 400 | 1.25 |
| SUNBRIGHT HGEO-150PA | 15000 | 8 | 0.94 | 0.25 | 400 | 1.25 |
| SUNBRIGHT HGEO-400PA | 40000 | 8 | 2.5 | 0.25 | 400 | 1.25 |

Addition of 20 microliters ([ICG-sulfo-OSu]=0.25 micromoles) of solution, ICG-sulfo-OSu in DMSO, to a solution (400 microliters), PEG in carbonate buffer, was performed. ICG-sulfo-OSu twice as much as $NH_2$ residue in the number of moles was allowed to react. The concentration of ICG-sulfo-OSu at the time of reaction was specified to be 0.6 mM. After rotational agitation was performed at room temperature for 24 hours under light shielding condition, the reaction solution was filtrated with a 0.22-micrometer syringe filter, so as to obtain a compound in which the near-infrared organic dye and the PEG were covalent-boned.

TABLE 2

| Product name of PEG employed | Sample name | Molecular weight of PEG | Form |
| --- | --- | --- | --- |
| GL2-200PA | MB2_20k-ICG | 20000 | monoamine branched chain |
| GL2-400PA | MB2_40k-ICG | 40000 | monoamine branched chain |
| GL2-600PA | MB2_60k-ICG | 60000 | monoamine branched chain |
| GL3-400PA 100U | MB3_50k-ICG | 50000 | monoamine branched chain |
| GL4-600PA | MB4_60k-ICG | 60000 | monoamine branched chain |

TABLE 2-continued
| Product name of PEG employed | Sample name | Molecular weight of PEG | Form |
|---|---|---|---|
| GL4-800PA | MB4_80k-ICG | 80000 | monoamine branched chain |
| PTE2-400EA | DB_40k-ICG2 | 40000 | diamine branched chain |
| PTE-400PA | TB_40k-ICG4 | 40000 | tetramine branched chain |
| HGEO-150PA | OB_15k-ICG8 | 15000 | octamine branched chain |
| HGEO-400PA | OB_40k-ICG8 | 40000 | octamine branched chain |
| ICG-Sulfo-OSu | ICG-Gly | | dye |
[Chem. 54]
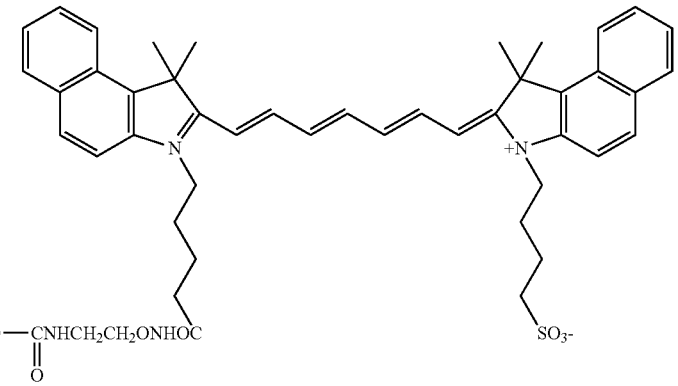
(40)
[Chem. 55]
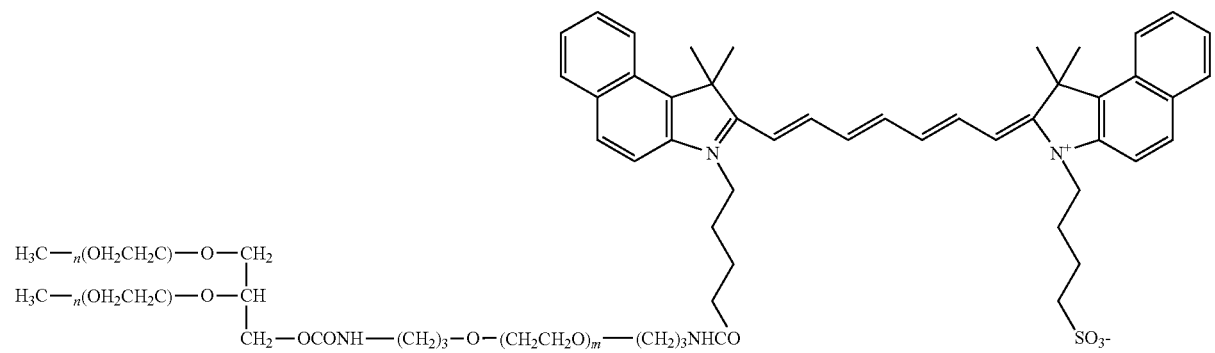
(41)
[Chem. 56]
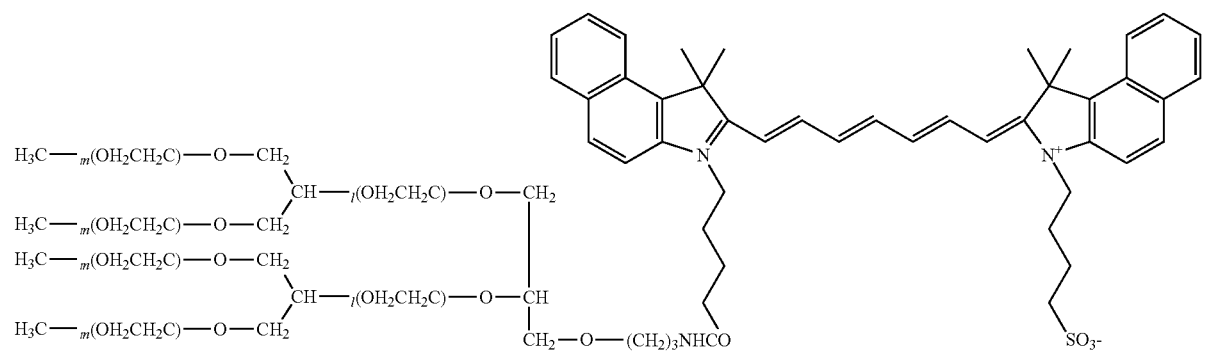
(42)
[Chem. 57]
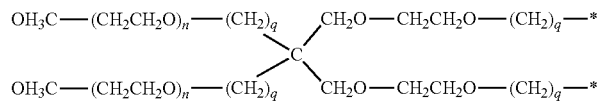
(43)

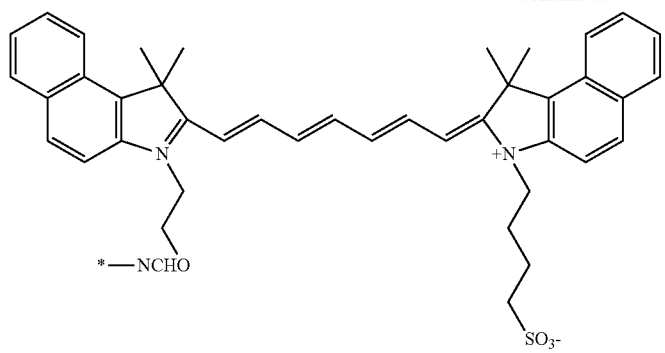
[Chem. 58]
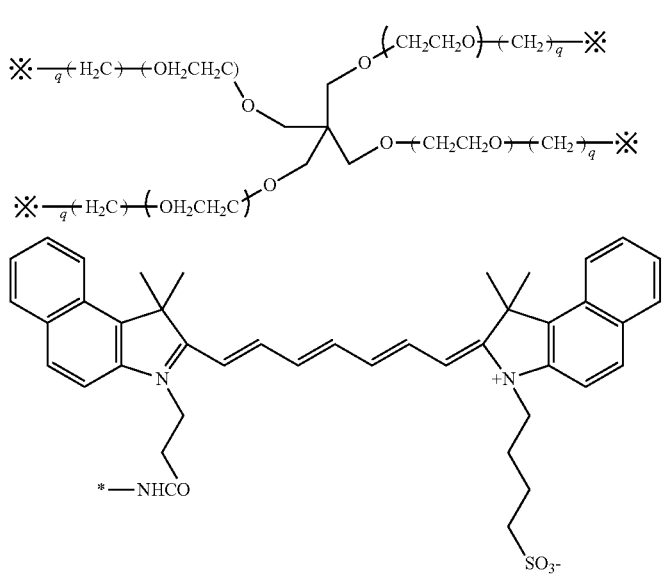
(44)
[Chem. 59]
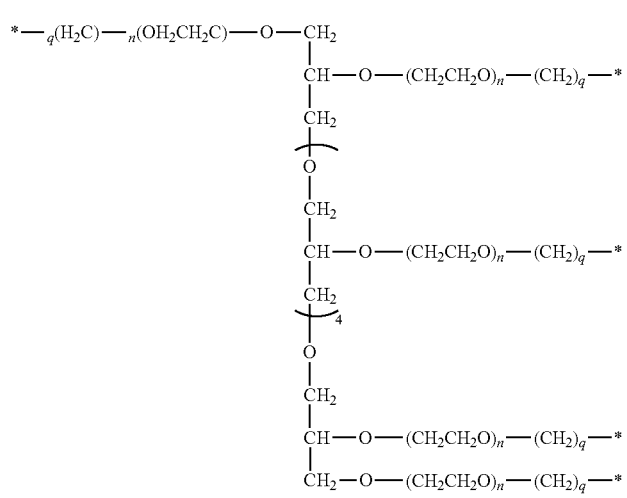
(45)

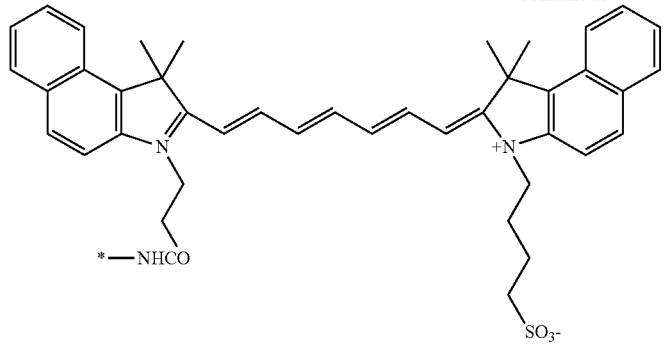

Example 2

Measurement of Absorption by Compound

Absorption spectra of MB2_40 k-ICG, MB3_50 k-ICG, MB4_80 k-ICG, TB_40 k-ICG4, OB_15 k-ICG8, OB_40 k-ICG8, and ICG-Gly in solutions were measured. Dilution was performed with 50 mM of 4-(2-hydroxyethyl)-1-piperazineethanesulfonic acid (HEPES) solution, and a maximum wavelength (lambda max) was measured on the basis of the absorption spectrum. Table 3 shows the results of respective absorption maximum wavelengths.

The absorption in the vicinity of 700 nm is absorption of a dye in an association state. Meanwhile, absorption in the vicinity of 785 nm is absorption by a near-infrared organic dye present as a monomer. It was made clear from the results shown in Table 3 that the compound, in which the branched chain PEG and the near-infrared organic dye were bonded, exhibited good dispersibility in water. On the other hand, it was indicated that ICG-Gly was unstable in the water because aggregates were observed in the water. Consequently, it was indicated that the stability of the near-infrared organic dye was improved by covalent-bonding with the PEG.

TABLE 3

| Sample name | Absorption maximum wavelength (lambda max) |
|---|---|
| MB2_40k-ICG | 721 nm, 786 nm |
| MB3_50k-ICG | 716 nm, 786 nm |
| MB4_80k-ICG | 720 nm, 787 nm |
| TB_40k-ICG4 | 719 nm, 783 nm |
| OB_15k-ICG8 | 716 nm, 782 nm |
| OB_40k-ICG8 | 716 nm, 782 nm |
| ICG-Gly | 682 nm |

Example 3

Evaluation of Retentivity of Compound in Blood

In order to examine the retentivity of the compound in blood, various compounds were administered to veins of nude mouse tails and the amounts of compounds remaining in blood were evaluated. Table 4 shows the list of compounds employed in the present example. The method for producing the compound was as described in Example 1. In Table 4, k represents 1,000. For example, 5 k represents 5,000.

TABLE 4

| Sample name | Product name of PEG employed | Molecular weight of PEG (molecular weight × the number) |
|---|---|---|
| MB2_20k-ICG | GL2-200PA | 20000 (10k × 2) |
| MB2_40k-ICG | GL2-400PA | 40000 (20k × 2) |
| MB2_60k-ICG | GL2-600PA | 60000 (30k × 1) |
| MB3_50k-ICG | GL3-400PA 100U | 50000 (10k × 1 + 20k × 2) |
| MB4_60k-ICG | GL4-600PA | 60000 (5k × 2 + 12.5k × 4) |
| MB4_80k-ICG | GL4-800PA | 80000 (5k × 2 + 17.5k × 4) |
| DB_40k-ICG2 | PTE2-400EA | 40000 (20k × 2) |
| TB_40k-ICG4 | PTE-400PA | 40000 (10k × 4) |

The retentivity of the compound in blood was evaluated as described below. Blood samples were taken from a mouse 1 hour, 3 hours, 1 day, 2 days, and 1 week after administration, and the fluorescent intensity of the blood was measured using IVIS (registered trademark) Imaging System 200 Series (produced by Caliper Life Science Inc.). The amount of administration to the mouse was 0.5 mg/kg in terms of the amount of dye. Table 5 shows the relative concentration in blood in the case where the concentration of ICG in blood 1 day after administration was specified to be 1. In addition, Table 6 shows changes in the relative concentration in blood with time in the case where the concentration of ICG in blood 1 day after administration was specified to be 1. As is shown in Tables 5 and 6, the PEG exhibited tendencies toward an improvement in the retentivity in blood along with an increase in the molecular weight thereof as compared with ICG and ICG-Gly serving as references. Meanwhile, reference samples, e.g., ICG and ICG-Gly, disappeared from the blood promptly. It is considered that access of serum protein to the near-infrared organic dye was limited by bonding the branched chain PEG to the near-infrared organic dye, accumulation into a liver was reduced and, as a result, the retentivity in blood was acquired.

TABLE 5

| Sample name | The number of $NH_2$ per PEG | Relative concentration in blood (1 day after administration) | Remarks |
|---|---|---|---|
| ICG | — | 1 | Dye (reference) |
| ICG-Gly | — | 14 | Dye (reference) |
| MB2_20k-ICG | 1 | 25 | monoamine branched chain |
| MB2_40k-ICG | 1 | 168 | monoamine branched chain |

TABLE 5-continued

| Sample name | The number of NH$_2$ per PEG | Relative concentration in blood (1 day after administration) | Remarks |
|---|---|---|---|
| MB2_60k-ICG | 1 | 267 | monoamine branched chain |
| MB3_50k-ICG | 1 | 246 | monoamine branched chain |
| MB4_60k-ICG | 1 | 207 | monoamine branched chain |
| MB4_80k-ICG | 1 | 304 | monoamine branched chain |
| DB_40k-ICG2 | 2 | 132 | diamine branched chain |
| TB_40k-ICG4 | 4 | 178 | tetramine branched chain |

TABLE 6

| Sample name | 1 hour after | 3 hours after | 1 day after | 2 days after | 1 week after |
|---|---|---|---|---|---|
| ICG | 36.7 | 19 | 1 | 0.89 | 0.72 |
| ICG-Gly | 90.5 | 43 | 13.8 | 12.5 | 5.7 |
| MB2_20k-ICG | 340.2 | 172.9 | 25.3 | 10.3 | 6.4 |
| MB2_40k-ICG | 329.7 | 293.3 | 168.2 | 93.6 | 11.9 |
| MB2_60k-ICG | 387.5 | 462.4 | 267.2 | 166.9 | 26.5 |
| MB3_50k-ICG | 365.3 | 364.7 | 246 | 152.6 | 22.4 |
| MB4_60k-ICG | 313.5 | 333.3 | 207.1 | 141.2 | 38.5 |
| MB4_80k-ICG | 463.9 | 414.7 | 304.2 | 183.1 | 41.4 |
| DB_40k-ICG2 | 309.7 | 291.8 | 132.7 | 63.5 | 14.4 |
| TB_40k-ICG4 | 355.1 | 346.4 | 177.6 | 71.3 | 11.2 |

Example 4

Tumor Accumulation of Compound

In order to evaluate the tumor accumulation of the compound, a contrast medium was administered to a tail vein of a tumor-bearing mouse which had been transplanted a colon 26 cell line. The amount of administration was 32 nmol in terms of the amount of dye. Then, tumor accumulation 1 day after administration of the contrast medium into the tumor-bearing mouse was evaluated by photoacoustic imaging and fluorescence. The photoacoustic imaging of the mouse was performed before administration of the contrast medium and 1 day after administration by employing a commercially available photoacoustic imaging apparatus (Nexus128, produced by Endra Inc.). The measurement wavelength was specified to be 797 nm. Subsequently, the relative photoacoustic signal intensity 1 day after administration relative to before administration was calculated. The amount of accumulation into a tumor of the mouse was evaluated using fluorescence, as described below. The mouse was euthanized with a carbon dioxide gas 24 hours after the administration. Thereafter, a tumor tissue was enucleated. The tumor tissue was transferred to a plastic tube, 1% Triton-X100 aqueous solution 1.25 times the tumor tissue in weight was added, and a homogenate was produced using a plastic pestle. Subsequently, dimethyl sulfoxide (DMSO) 20.25 times the tumor tissue in weight was added. The amount of dye in the tumor tissue was quantified by using IVIS (registered trademark) Imaging System 200 Series (produced by Caliper Life Science Inc.) and measuring the fluorescent intensity of the homogenate solution in the state of the plastic tube. The proportion of the amount of migration of the dye relative to the amount of administration (% injected dose: abbreviated to % ID) per unit weight of the tumor tissue was calculated as the amount of tumor accumulation of the compound (% ID/g). The results thereof are shown in Table 7.

It was indicated that the tumor accumulation of ICG bonded to the branched chain PEG increased along with an increase in the molecular weight as compared with the tumor accumulation of ICG and ICG-Gly serving as reference. In addition, it was indicated that the molecular weight and the form of PEG were important parameters with respect to the tumor accumulation.

TABLE 7

| Sample name | Relative photoacoustic intensity (1 day after administration) | Amount of tumor accumulation (% ID/g) |
|---|---|---|
| ICG | 1 | 0.1 |
| ICG-Gly | 1.9 | 0.4 |
| MB2_20k-ICG | 2.0 | 12.3 |
| MB2_80k-ICG | 6.2 | 17.8 |

Example 5

Modification of PEG Including Capture Molecule (Affibody (registered trademark))

Branched PEGs used in the present example were dimaleimide branched PTE2-200MA2 (produced by NOF CORPORATION, MW 20,000) and dimaleimide branched PTE2-400MA2 (produced by NOF CORPORATION, MW 40,000).

A dithiothreitol (DTT) solution was added to a solution (produced by Affibody) of Affibody (registered trademark) to be bonded to HER2 in such a way that the final concentration became 20 mM, and a reduction treatment was performed at 25 degrees Celsius for 2 hours under light shielding condition. DTT was removed from the reaction solution by using a PD-10 column (produced by GE Healthcare). Dimaleimide branched PTE2-200MA2 (produced by NOF CORPORATION, MW 20,000) and dimaleimide branched PTE2-400MA2 (produced by NOF CORPORATION, MW 40,000) were weighed into 1.5-mL plastic tubes independently. The weighed PEG was diluted with a phosphate buffer not containing EDTA to become 143 micromolars and was mixed with Affibody (registered trademark) subjected to the above-described reduction treatment and, then, a reaction was induced at 25 degrees Celsius for 15 hours or more. The reaction molar ratio (Affibody (registered trademark)/PEG) was specified to be 2 on a charge basis. A solution (12.5 mM), ICG-Sulfo-OSu in DMSO, was mixed with the above-described mixed solution of Affibody (registered trademark) and PEG, and a reaction was induced at 25 degrees Celsius for 2 hours. The reaction molar ratio (ICG-Sulfo-OSu/Affibody (registered trademark)) was specified to be 1 on a charge basis. The resulting solution was filtrated with a filter (pore size 1.2 micrometers) and, thereafter, Affibody (registered trademark) not bonded to the PEG was removed by ultrafiltration using Amicon Ultra-4 (produced by Nihon Millipore K.K.) having a pore size of 10 kDa, so as to obtain PEGs modified with ICG and Affibody (registered trademark). Among the thus obtained compounds, the compound by using PTE2-200MA2 is abbreviated to Af-PTEPEG20 and the compound by using PTE2-400MA2 is abbreviated to Af-PTEPEG40.

Evaluation of Bonding Property of PEG Including Capture Molecule to HER2

The bonding property of the PEG including the capture molecule to HER2 serving as a target molecule was evaluated by a surface plasmon resonance method (SPR). In SPR, the measurement was performed using Proteon (registered trademark) XPR36 (produced by Bio-Rad Laboratories). Recombinant Human ErbB2/Fc Chimera (produced by R&D Systems) was dissolved into an acetate buffer (pH 5.0), and was immobilized by amine coupling to a carboxyl group on the GLM sensor chip surface. The amount of immobilization was about 3,000 RU (Resonance Unit). Subsequently, the PEG including the capture molecule was diluted to various concentrations with a phosphate buffer (pH 7.4) containing 0.005% of Tween20 and was injected into a flow cell at a flow rate of 50 microliters/min. As for the measurement times, an injection time (bonding) was 120 seconds and an elapsed time after stopping of injection (dissociation) was 120 seconds. In a bonding kinetic analysis experiment, sensor grams were analyzed using 1:1 Langmuir fitting model. The calculated binding dissociation constants ($K_D$) are collectively shown in Table 8. The bonding property to HER2 was ensured with respect to every sample.

TABLE 8

| Sample name | Product name of PEG employed | Type of capture molecule | Molecular weight of PEG | $K_D$ [nM] |
|---|---|---|---|---|
| Af-PTEPEG20 | PTE2-200MA2 | Affibody (registered trademark) | 20000 | 23.8 |
| Af-PTEPEG40 | PTE2-400MA2 | Affibody (registered trademark) | 40000 | 44.7 |

Evaluation of Tumor Accumulation of PEG Including Capture Molecule

In the evaluation of tumor accumulation, female outbred line BALB/c Slc-nu/nu mouse (6 week-old at the time of purchase) (Japan SLC Inc.) was used. The mouse was adapted to an environment in which a diet and drinking water were able to be consumed freely for a week before the mouse was transplanted a tumor, while standard diet and bed were employed. About 1 week before an imaging experiment, $1\times10^6$ of Colon 26 mouse colon cancer cells (RIKEN) were subcutaneously injected into each of the right shoulder and the right thigh of the mouse and $1\times10^6$ of Colon 26 mouse colon cancer cells containing artificially introduced HER2 genes were subcutaneously injected into each of the left shoulder and the left thigh of the mouse. All tumors became established until the experiment and the weights of the mice were 17 to 22 g. An intraveneous injection of 200 microliters (13 nmol in terms of ICG) of PEG including the capture molecule or MB3_50 k-ICG into tumor-bearing mice was performed. The mice were euthanized with a carbon dioxide gas 24 hours after the administration. Subsequently, each cancer tissue was enucleated. The cancer tissue was transferred to a plastic tube, 1% Triton-X100 aqueous solution 1.25 times the cancer tissue in weight was added, and a homogenate was produced using a plastic pestle. Thereafter, DMSO 20.25 times the cancer tissue in weight was added, so as to prepare a solution of dye extracted from the tumor tissue. Meanwhile, cancer tissue was enucleated from the tumor-bearing mouse not administered the PEG including the capture molecule. The cancer tissue was transferred to a plastic tube, 1% Triton-X100 aqueous solution 1.25 times the cancer tissue in weight was added, and a homogenate was produced using a plastic pestle, so as to prepare a Triton X100 solution containing the tumor tissue. Then, the solution of a known concentration of PEG including the capture molecule was diluted to various concentrations with the above-described Triton-X100 solution containing the cancer tissue. A standard solution for calibration was prepared by adding DMSO 20.25 times the resulting diluted solution in amount. The amount of dye in the cancer tissue was quantified by using IVIS (registered trademark) Imaging System 200 Series (CALIPER) and measuring the fluorescent intensity of the solution of dye extracted from the tumor tissue and the standard solution for calibration in the state of the plastic tube.

In the above-described evaluation of the tumor accumulation, just before the mouse was euthanized with a carbon dioxide gas 24 hours after the administration, blood was taken from the tail vein. The resulting blood was transferred to a plastic tube, 1% Triton-X100 aqueous solution 4.5 times the blood in volume was added. Thereafter, DMSO 4.5 times the blood in volume was added, so as to prepare a blood-containing solution. The fluorescent intensity of the blood-containing solution was measured by using IVIS (registered trademark) Imaging System 200 Series (CALIPER) in the state of the plastic tube. Meanwhile, the particle solution having a known concentration was diluted to various concentrations with the 1% Triton-X100 aqueous solution. The diluted particle solution and an equal amount of blood taken from a mouse not administered were mixed. Subsequently, 1% Triton-X100 aqueous solution was added in such a way that the volume including the volume of the above-described diluted particle solution became 4.5 times the volume of blood. Then, a blood particle solution for calibration curve was produced by adding DMSO 4.5 times the blood in volume. The fluorescent intensity was measured and a calibration curve was formed as with the taken blood sample. Next, the concentration in the blood was calculated by using the fluorescent intensity of the blood-containing solution and the calibration curve formed. Each of the calculated concentrations in the blood was divided by the total amount of administration, so as to calculate the proportion of the abundance in the blood per amount of administration (% ID).

Figure 2:
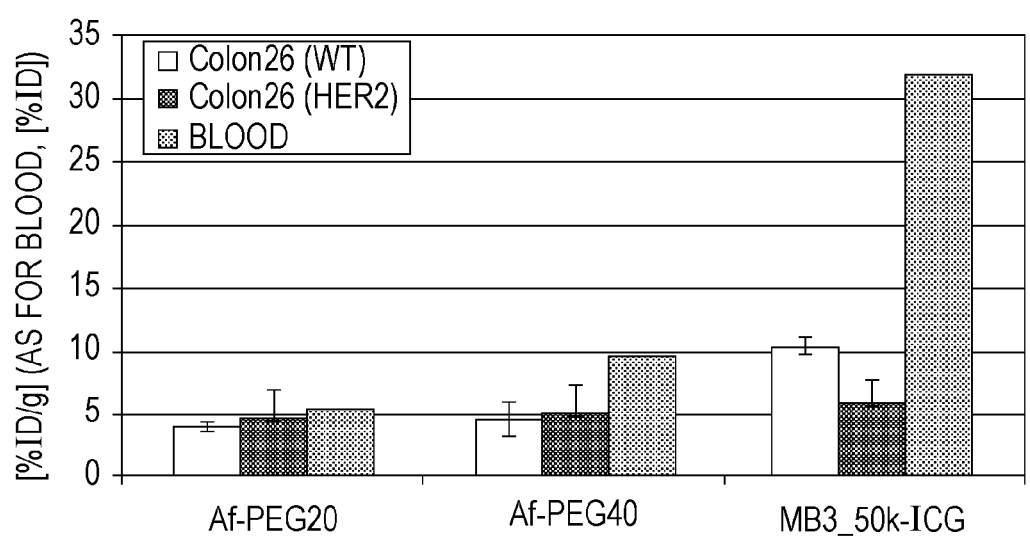
FIG. 2 is a graph showing the results obtained in an evaluation experiment of the tumor accumulation performed in an example according to an aspect of the present invention.

The results of the tumor accumulation and the results of the abundance in the blood are summarized in FIG. 2. All the PEGs including the capture molecule exhibited tendencies toward a decrease in the abundance in the blood and, along with that, a decrease in the tumor accumulation as compared with MB3_50 k-ICG. In addition, ratios of the amount of accumulation into the Colon 26 mouse colon cancer cells containing artificially introduced HER2 genes relative to the amount of accumulation into the Colon 26 mouse colon cancer cells were calculated and are summarized in Table 9. The amounts of accumulation of all the PEGs including the capture molecule into the Colon 26 mouse colon cancer cells containing artificially introduced HER2 genes were large as compared with those of MB3_50 k-ICG. Therefore, an effect of the capture molecule on the property to bond to HER2 was ascertained.

TABLE 9

| Sample name | Colon26 (HER2)/Colon26 (WT) Ratio of amount of tumor accumulation |
|---|---|
| Af-PTEPEG20 | 1.16 |
| Af-PTEPEG40 | 1.13 |
| MB3_50k-ICG | 0.57 |

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2012-161641, filed Jul. 20, 2012, which is hereby incorporated by reference herein in its entirety.

The invention claimed is:

1. A compound represented by any one of formula (1) to formula (6):

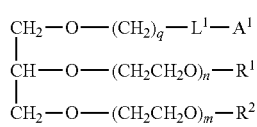
(1)

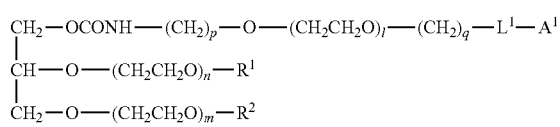
(2)

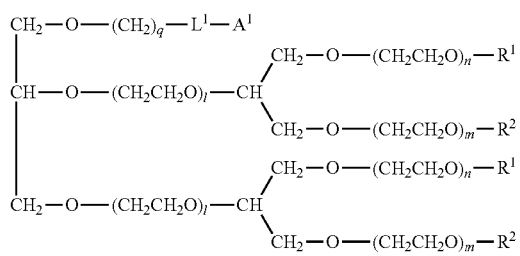
(3)

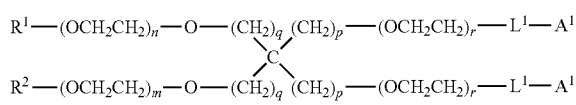
(4)

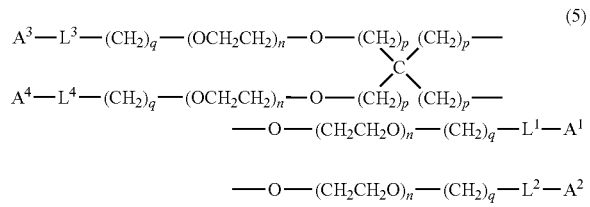
(5)

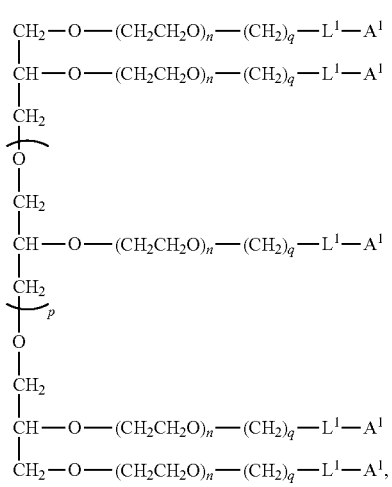
(6)

wherein, in the formula (1), $A^1$ represents an organic dye which absorbs light in a near-infrared wavelength region, $L^1$ represents a linker part which is any one of —NH—, —CO—, —O—, and —S— or which contains at least one of —NH—, —CO—, —O—, and —S—, q represents an integer of 1 to 5, m and n represent independently an integer of 10 or more and 2,500 or less, and $R^1$ and $R^2$ represent independently an alkyl group having 1 to 5 carbon atoms, wherein, in the formula (2), $A^1$ represents an organic dye which absorbs light in the near-infrared wavelength region, $L^1$ represents a linker part which is any one of —NH—, —CO—, —O—, and —S— or which contains at least one of —NH—, —CO—, —O—, and —S—, p and q represent independently an integer of 1 to 5, l, m, and n represent independently an integer of 10 or more and 2,500 or less, and $R^1$ and $R^2$ represent independently an alkyl group having 1 to 5 carbon atoms, wherein, in the formula (3), $A^1$ represents an organic dye which absorbs light in the near-infrared wavelength region, $L^1$ represents a linker part which is any one of —NH—, —CO—, —O—, and —S— or which contains at least one of —NH—, —CO—, —O—, and —S—, q represents an integer of 1 to 5, l, m, and n represent independently an integer of 10 or more and 2,500 or less, and $R^1$ and $R^2$ represent independently an alkyl group having 1 to 5 carbon atoms, wherein, in the formula (4), $A^1$ and $A^2$ represent independently an organic dye which absorbs light in the near-infrared wavelength region, $L^1$ and $L^2$ represent independently a linker part which is any one of —NH—, —CO—, —O—, and —S— or which contains at least one of —NH—, —CO—, —O—, and —S—, p, q and r represent independently an integer of 1 to 5, m and n represent independently an integer of 10 or more and 2,500 or less, and $R^1$ and $R^2$ represent independently an alkyl group having 1 to 5 carbon atoms, wherein, in the formula (5), $A^1$, $A^2$, $A^3$, and $A^4$ represent independently an organic dye which absorbs light in the near-infrared wavelength region, $L^1$, $L^2$, $L^3$, and $L^4$ represent independently a linker part which is any one of —NH—, —CO—, —O—, and —S— or which contains at least one of —NH—, —CO—, —O—, and —S—, p and q represent independently an integer of 1 to 5, and n represents an integer of 10 or more and 2,500 or less, and wherein, in the formula (6), $A^1$ represents an organic dye which absorbs light in the near-infrared wavelength region, $L^1$ represents a linker part which is any one of —NH—, —CO—, —O—, and —S— or which contains at least one of —NH—, —CO—, —O—, and —S—, p and q represent independently an integer of 1 to 5, and n represents an integer of 10 or more and 2,500 or less wherein, in the formulae (1) to (6), $A^1$, $A^2$, $A^3$, and $A^4$ are independently represented by any one of formulae (7) and (8):

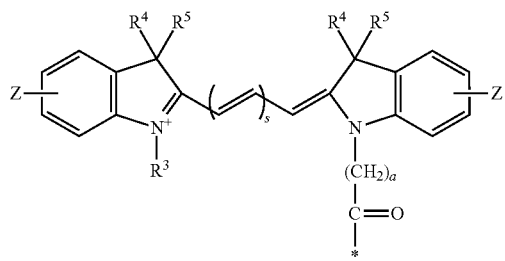

(7)

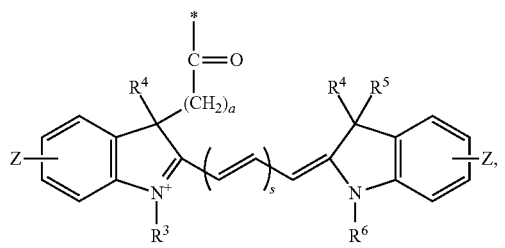

(8)

wherein, in the formula (7) and in the formula (8), the symbol * represents a bond with any one of $L^1$, $L^2$, $L^3$, and $L^4$ in the formulae (1) to (6), wherein, in the formula (7) and in the formula (8), Z forms a cyclic aromatic ring composed of a benz[e]indole ring, benz[f]indole ring, or benz[g]indole ring together with a hydrogen atom, a sulfonate group, or an indole ring bonded to Z, and furthermore, a hydrogen atom of the cyclic aromatic ring may be substituted with an alkyl group having 1 to 10 carbon atoms, an alkoxy group having 1 to 10 carbon atoms, or a sulfonate group, wherein, in the formula (7) and in the formula (8), $R^3$ represents any one of an alkyl group having 1 to 10 carbon atoms and —$(CH_2)_b$—$SO_3^-$ where b represents an integer of 1 to 10, and when $R^3$ is an alkyl group, a halogen ion or an organic acid ion may be contained as a counter ion, and $R^4$ and $R^5$ represent independently any one of a hydrogen atom, an alkyl group having 1 to 10 carbon atoms, an alkoxy group having 1 to 10 carbon atoms, —$(CH_2)_b$—$SO_3^-$, where b represents an integer of 1 to 10, and —$(CH_2)_b$—$SO_3X$, where b represents an integer of 1 to 10 and X represents any one of sodium, potassium, ammonium, triethylammonium, lysine, and arginine, wherein, in the formula (7) and in the formula (8), a represents an integer of 1 to 10 and s represents 2 or 3, and wherein, in the formula (8), $R^6$ represents any one of an alkyl group having 1 to 10 carbon atoms, —$(CH_2)_b$—$SO_3^-$, where b represents an integer of 1 to 10, —$(CH_2)_b$—$SO_3X$ where b represents an integer of 1 to 10 and X represents any one of sodium, potassium, ammonium, triethylammonium, lysine, and arginine.

2. The compound according to claim 1, further comprising a capture molecule.

3. The compound according to claim 1, wherein, in the formulae (1) to (6), at least one linker part of $L^1$ to $L^4$ is a polypeptide or a single-chain antibody.

4. The compound according to claim 1, wherein, in the formulae (1) to (6), at least one of $L^1$ to $L^4$ is represented by formula (46):

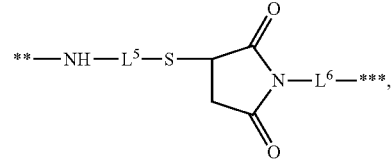

(46)

where $L^5$ represents a polypeptide or a single-chain antibody, —NH— represents a bond through an amino group of an amino acid in the polypeptide or the single-chain antibody, —S— represents a bond through a thiol group of an amino acid in the polypeptide or the single-chain antibody, $L^6$ represents an alkyl chain having 1 to 10 carbon atoms and including any one of a carbonyl group, an amide group, an ester group and a piperazyl group,  represents a bond with at least one of $A^1$ to $A^4$, * represents a bond with the alkyl chain side or the ethylene glycol chain side of the formulae (1) to (6).

5. The compound according to claim 4, wherein, in the formula (46), $L^6$ is —$(CH_2)_2$—C(=O)—NH—, where the ethylene group side is bonded to a nitrogen atom of a maleimide group and the amide group side is bonded at ***.

6. The compound according to claim 1, wherein the compound is suitable for imaging a tumor.

7. The compound according to claim 1, wherein the compound is suitable for imaging a lymph node.

8. A photoacoustic imaging contrast medium comprising the compound according to claim 1 and a dispersion medium.

9. The photoacoustic imaging contrast medium according to claim 8, further comprising an addition agent.

* * * * *